US011622976B2

(12) United States Patent
Wada et al.

(10) Patent No.: US 11,622,976 B2
(45) Date of Patent: Apr. 11, 2023

(54) URINE ALKALI AGENT USEFUL FOR TREATMENT OF CANCER PATIENT

(71) Applicant: Delta-Fly Pharma, Inc., Tokushima (JP)

(72) Inventors: Hiromi Wada, Kyoto (JP); Kiyoshi Eshima, Tokushima (JP); Tatsuhiro Ishida, Tokushima (JP); Reo Hamaguchi, Tokyo (JP)

(73) Assignee: Delta-Fly Pharma, Inc., Tokushima (JP)

( * ) Notice: Subject to any disclaimer, the term of this patent is extended or adjusted under 35 U.S.C. 154(b) by 0 days.

(21) Appl. No.: 16/962,990

(22) PCT Filed: Nov. 22, 2018

(86) PCT No.: PCT/JP2018/043099
§ 371 (c)(1),
(2) Date: Jul. 17, 2020

(87) PCT Pub. No.: WO2019/142490
PCT Pub. Date: Jul. 25, 2019

(65) Prior Publication Data
US 2020/0368273 A1 Nov. 26, 2020

(30) Foreign Application Priority Data

| Jan. 19, 2018 | (JP) | JP2018-007303 |
| May 24, 2018 | (JP) | JP2018-099667 |
| Oct. 19, 2018 | (JP) | JP2018-197447 |

(51) Int. Cl.
*A61K 33/00* (2006.01)
*A61P 35/00* (2006.01)
*A61K 9/00* (2006.01)
*A61K 31/194* (2006.01)
*A61K 9/08* (2006.01)
*A61K 31/716* (2006.01)
*C07K 16/28* (2006.01)

(52) U.S. Cl.
CPC ............ *A61K 33/00* (2013.01); *A61K 9/0014* (2013.01); *A61K 9/0053* (2013.01); *A61K 31/194* (2013.01); *A61P 35/00* (2018.01); *A61K 9/08* (2013.01); *A61K 31/716* (2013.01); *C07K 16/2818* (2013.01)

(58) Field of Classification Search
CPC ..................................................... A61K 33/00
USPC ......................................................... 424/717
See application file for complete search history.

(56) References Cited

U.S. PATENT DOCUMENTS

| 6,565,881 B1* | 5/2003 | Nurnberg et al. | A61K 8/738 424/466 |
| 2005/0158375 A1* | 7/2005 | Kimura | A61K 47/6911 424/450 |
| 2007/0166401 A1 | 7/2007 | Park | |
| 2008/0038376 A1 | 2/2008 | Giles | |
| 2011/0300227 A1 | 12/2011 | Danhof | |
| 2014/0288143 A1 | 9/2014 | Nuijen et al. | |
| 2015/0293100 A1* | 10/2015 | Gomis | A61P 35/00 435/6.12 |
| 2015/0320754 A1* | 11/2015 | Kutok | A61K 31/52 424/278.1 |
| 2017/0296578 A1* | 10/2017 | Sampson | A61K 9/0014 |
| 2019/0350952 A1 | 11/2019 | Levitt | |
| 2020/0138855 A1 | 5/2020 | Wada et al. | |

FOREIGN PATENT DOCUMENTS

| CN | 1708310 A | 12/2005 |
| CN | 102429887 A | 5/2012 |
| CN | 103316035 A | 9/2013 |
| CN | 109641055 A | 4/2019 |
| EP | 3 456 354 A1 | 3/2019 |
| IT | SA960003 A1 | 8/1997 |
| JP | 2003-055297 A | 2/2003 |
| JP | 6359198 B1 | 6/2018 |
| TW | 201141501 A | 12/2011 |
| WO | WO 2013/067449 A1 * | 5/2013 |
| WO | WO 2014/043510 A1 * | 3/2014 |
| WO | WO 2016/112466 A1 * | 7/2016 |
| WO | WO 2018/049000 A1 * | 3/2018 |
| WO | WO-2019/016928 A1 | 1/2019 |

OTHER PUBLICATIONS

Azzarito et al (PLOS ONE, 2016, 11(7)(e0159763): 13 pages).*
Hamid et al (NEJM, 2013, 369(2): 134-144).*
Ina et al (Anti-Cancer Agents in Medicinal Chemistry, 2013, 13: 681-688).*
Ikeda et al (European Journal of Cancer Care, 2005, 14: 425-439).*
Mennie et al (The Lancet, 1975, 306: 942-943).*
Taguchi (International Journal of Immunopharmacology, 1982, 4(4): p. 271).*
Cardone et al. "The Role of Disturbed Ph Dynamics and the NA /H Exchanger in Metastasis," Nature Reviews Cancer, Oct. 2005, 5:786-795.
Decision of Refusal dated Mar. 3, 2020 in JP 2019-527262, with English translation.
Faes et al., "Acidic tumor microenvironment abrogates the efficacy of mTORC1 inhibitors," Molecular Cancer, 2016, 15:78(1-11).
Hamaguchi et al., "Effects of an Alkaline Diet on EGFR-TKI Therapy in EGFR Mutation-positive NSCLC," Anticancer Research, 2017, 37:5141-5145.

(Continued)

*Primary Examiner* — Sean E Aeder
(74) *Attorney, Agent, or Firm* — Foley & Lardner LLP

(57) ABSTRACT

An object of the present invention is to provide a highly effective method for treatment/remission of cancer, and prevention of recurrence/metastasis of cancer at low cost and with few side effects. A composition containing a urinary alkalinization agent, for use in treatment or remission of cancer, or prevention of recurrence or metastasis of cancer.

24 Claims, 16 Drawing Sheets

(56) References Cited

OTHER PUBLICATIONS

Harguindy et al., "The role of pH dynamics and the Na/H antiporter in the etiopathogenesis and treatment of cancer. Two faces of the same coin-one single nature," Biochimica et Biophysica Acta, Jul. 19, 2005, 1756, 1-24.

International Search Report dated Feb. 26, 2019 in PCT/JP2018/043099.

Ito et al., "Measures for tumor lysis syndrome targeted at patients with acute leukemia," Journal of Japanese Society of Hospital Patients, 2011, 47(7):823-826, with English translation.

Kobayashi et al., "Biweekly administration of irinotecan (CPT-11) plus cisplatin with an antidiarrheal program of intestinal alkalization to reduce diarrhea in cancer patients," Ann. Cancer Res. Ther., 2012, 20(2):52-57.

Office Action dated Aug. 6, 2019 in JP 2019-527262, with English translation.

Office Action dated Dec. 19, 2019 in JP 2019-527262, with English translation.

Pilon-Thomas et al., "Neutralization of Tumor Acidity Improves Antitumor Responses to Immunotherapy," Cancer Research, 2016, 76(6):1381-1390.

Robey et al., "Bicarbonate Increases Tumor pH and Inhibits Spontaneous Metastases," Cancer Research, Mar. 10, 2009, 69(6):2260-2268.

Schlanger et al., "Cancer Tumors Thought to be Caused by Molds," Wondermakers Articles, Dec. 10, 2008, 2 pages.

Silva et al., "The Potential Role of Systemic Buffers in Reducing Intratumoral Extracellular pH and Acid-Mediated Invasion," Cancer Research, Mar. 15, 2009, 69(6):2677-2684.

Alqahtani S, et al., Introduction of apoptosis and cytokine markers in colon cancer cells by magnesium oxide (MgO) nanoparticles, Toxicological & Environmental Chemistry, Feb. 7, 2017, vol. 99, No. 2, pp. 302-314 (14 pages).

Extended European Search Report issued for EP Appl. Ser. No. 18900871 dated Aug. 25, 2021 (8 pages).

Office Action dated Oct. 10, 2022 in CN 201880086699.4, with English translation.

* cited by examiner (A)

(B)

Sep-15　　　　　　　　　May-16

(A)

(B)

Jan-11    Jun-13

(A)

Jan-16          Sep-16

(B)

(A) August, 2017

(B) February, 2018

──▲── (1) Citric acid beverage containing citric acid, sodium citrate, calcium lactate ··◆·· (2) Gastrointestinal medicine containing H2 blocker ──✕── (3) Gastrointestinal medicine containing proton pump inhibitor (C)

(D)

(A) April 28, 2017

(B) July 2, 2018

URINE ALKALI AGENT USEFUL FOR TREATMENT OF CANCER PATIENT

CROSS-REFERENCE TO RELATED APPLICATIONS

This application is the U.S. National Stage of PCT/JP2018/043099, filed Nov. 22, 2018, which claims priority to JP 2018-007303, filed Jan. 19, 2018.

TECHNICAL FIELD

The present invention relates to use of a urinary alkalinization agent for treatment or remission of cancer, or prevention of recurrence or metastasis of cancer.

BACKGROUND ART

Recently, it has been confirmed/reported that cancer immunotherapy using an immune checkpoint inhibitor (trade name: Opdivo (registered trademark)), which contains an anti-human PD-1 monoclonal antibody (nivolumab) as an active ingredient, is highly effective in treating various cancers. Such a cancer immunotherapy has attracted attention as a new cancer therapy following conventional therapies using a cytotoxic anti-cancer agent and a cancer molecular targeted drug.

In the meantime, Opdivo is an extremely expensive medicament (the medication cost/person/year exceeds 20 million yen). The medication cost imposes a heavy burden on patients and the finances of the medical insurance systems of national/local governments. In addition, the medical-care expenditure is estimated to continuously increase in the future with rapid aging of the population and medical advances.

For the reason, it is strongly desired to develop a highly effective method for treating/preventing cancer at low cost.

Usually, the intracellular pH (hereinafter referred to as "pHi") of normal cells is 6.9 to 7.2; whereas the extracellular pH (hereinafter referred to as "pHe") is 7.3 to 7.4; in short, the pHe of normal cells is alkalinity compared to pHi thereof. Conversely, the pHi of cancer cells is 7.1 to 7.6; whereas, pHe is 6.2 to 6.9; the pHe of cancer cells is acidity compared to pHi thereof, in short, the pH gradient (relationship between pHi and pHe) of cancer cells is opposite to that of the normal cells. In cancer cells, compared to normal cells, the glycolysis system is up-regulated, with the result that lactic acid and protons (hydrogen ions) are produced in a large amount. The lactic acid produced is aggressively discharged outside the cells by a monocarboxylic acid transporter (MCT) and protons by $Na^+/H^+$ exchange carrier 1 (NHE-1), $Na^+$ dependent $HCO_3^-/Cl^-$ exchanger and/or $H^+$/lactic acid co-transporter. As a result, the pHe of cancer cells is acidic compared to pHi. In the cells where pHi is high and NHE-1 is activated, malignant transformation of cells, cell proliferation, expression of an oncogene, activation of a growth factor, activation of glycolysis, promotion of DNA synthesis, acceleration of cell cycle, decrease of apoptosis induction, migration of cells, angiogenesis, metastasis of cancer and increase of drug resistance occur, according to the research report (Non Patent Literature 1).

In cancer cells, NHE-1 is activated to promote formation of pseudopodia and accelerate assembling of lysosomes containing a proteolytic enzyme to a pseudopodium tip. If NHE-1 is further activated, cancer cells change into amoeba-like cells and secretion of a proteolytic enzyme from the lysosomes localized is accelerated, with the result that cancer cells are allowed to easily invade into outside of tissues and proliferation of cancer cells is promoted, according to the research report (Non Patent Literature No. 2).

Up to present, there is a research reporting that when the pHe of cancer cells is shifted from an acidic pH range to alkaline pH range by gradually increasing the concentration of sodium hydrogen carbonate in the serum, the proliferation and invasion of cancer cells can be suppressed (Non Patent Literature 3).

There is another research reporting that when a C57B/6 mouse group is fed with an aqueous solution of sodium hydrogen carbonate (200 mmol/L (17 g/L)) for 3 days, and then, subcutaneously transplanted with B16 melanoma cells at the left lateral region of the abdomen, and subjected to a cancer immunotherapy by, e.g., a cancer immunity-checkpoint inhibitor while feeding an aqueous solution of sodium hydrogen carbonate, a significantly high antitumor effect is obtained, compared to a mouse group fed with water containing no sodium hydrogen carbonate (Non Patent Literature 4).

There is another research reporting that when a C57B/6 mouse group is fed with an aqueous solution of sodium hydrogen carbonate (200 mmol/L (17 g/L)) for 3 days, and then, subcutaneously transplanted with HT29 human cancer cell strain at the left lateral region of the abdomen, and administered with a cancer molecular targeted drug, rapamycin, which is an inhibitor for mTORC1 (Mechanistic Target of Rapamycin Complex-1) while feeding an aqueous solution of sodium hydrogen carbonate, a significantly high antitumor effect is obtained, compared to a mouse group fed with water containing no sodium hydrogen carbonate (Non Patent Literature 5).

When patients with advanced non-small cell lung cancer having a mutation in EGFR (epidermal growth factor receptor) gene were administered with EGFR-TKI (epidermal growth factor receptor-tyrosine kinase inhibitor) such as gefitinib, erlotinib and afatinib and the life extension effect on the patients was analyzed. In the analysis, it was suggested that patients fed with an alkaline diet (diet reduced in meat, which likely produces uric acid in vivo, and mainly consisting of fruits and vegetables containing a citrate, a succinate and a malate, which likely produce a hydrogen carbonate, in vivo) were found to have alkaline urine, which may possibly contribute to life extension (Non Patent Literature 6).

However, up to present, a clinically evidence clearly showing that a treatment with an alkalinization agent such as sodium hydrogen carbonate is effective for treatment or remission of cancer in patients, has not been obtained. The cancer growth inhibitory action, which is exhibited by an animal model obtained by grafting cancer cells to an immunodeficient mouse, cannot be used for directly predicting an effect (for example, not only a local effect such as shrinkage of cancer but also the exhaustive effect on the condition of a cancer patient, such as a life extension effect) exerted in cancer patients. In other words, it is difficult to predict the effect exerted in cancer patients based on the test results of cancer-bearing mouse models. For the reason, the test results using the above C57B/6 mice do not disclose any specific method for clinically applying an aqueous solution of sodium hydrogen carbonate as an anti-cancer agent to humans.

Sodium hydrogen carbonate is contained in commercially available OTC drugs for treating e.g., excessive gastric acid and heartburn as an active ingredient in a dose of 500 mg to 1500 mg/time/adult. Examples of the OTC drugs include, Japanese Pharmacopoeia-listed sodium hydrogen carbonate (manufactured by Kenei Pharmaceutical Co., Ltd.), Ohta's Isan (manufactured by Ohta's Isan Co., Ltd.) and Panciron G (ROHTO Pharmaceutical Co., Ltd.). These drugs containing sodium hydrogen carbonate are known as a therapeutic agent for, e.g., excessive gastric acid and heartburn and not known as agent effective for treating cancer and preventing metastasis/recurrence.

Magnesium oxide is usually used as a laxative (for example, Magmitt (manufactured by Kyowa Chemical Industry Co., Ltd.), Magnesium Oxide E laxative (manufactured by Kenei Pharmaceutical Co., Ltd.)). However, it is not known that these laxatives containing magnesium oxide are effective for treating cancer and preventing metastasis/recurrence.

Citric acid is contained in health foods (for example, a plum extract) having a fatigue recovery-effect and sold for the general public. However, it is not known that these health foods containing citric acid are effective for treating cancer and preventing metastasis/recurrence.

It is said that hot springs containing hydrogen carbonate (sodium bicarbonate) present in various places in Japan are effective for treating e.g., cut, burn, chronic dermatitis, atopic dermatitis, allergic disease and rheumatism, due to hydrogen carbonate ions absorbed from the skin. However, it is not known that these hot springs are effective for treating cancer and preventing metastasis/recurrence.

Further, some of commercially available bath additives (for example, Bub (manufactured by Kao Corp.) and medicated foam bath (Lion Chemical Co., Ltd.)) contain carbonate as an active ingredient. In these bath additives, a weakly alkaline sodium hydrogen carbonate powder and a weakly acidic citric acid powder are mixed in hot-water bath and neutralized with each other while dissolving in hot water to generate bubbles of carbon dioxide in the hot-water bath. The pH value of the hot water at this time is maintained at around 7 (neutral). It is said that the bath additives have effect-efficacies on, e.g., cut, burn, chronic dermatitis, atopic dermatitis, allergic disease and rheumatism due to hydrogen carbonate ions absorbed from the skin; however, there are no reports that the bath additives are effective for treating cancer and preventing metastasis/recurrence.

CITATION LIST

Non Patent Literatures

Non Patent Literature No. 1: S. Harguindey et al., Biochimica et Biophysica Acta 1756 (2005): 1-24

Non Patent Literature No. 2: Rosa A. Cardone et al., Nature Reviews, Cancer 5 (2005): 786-795

Non Patent Literature No. 3: Ariosto S. Silva et al., Cancer Research 69 (2009): 2677-2684

Non Patent Literature No. 4: Shari Pilon-Thomas, et al., Cancer Research Science 76 (2016): 1381-1390

Non Patent Literature No. 5: Serina Faes et al., Molecular Cancer (2016)15: 78

Non Patent Literature No. 6: Reo Hamaguch et al., Anticancer Research 37 (2017): 5141-5145

SUMMARY OF INVENTION

Technical Problem

As described above, medical-care expenditure is continuously increasing with rapid aging of the population and medical advances, and imposes a heavy burden on patients and the finances of the medical insurance systems of national/local governments.

In the circumstances, an object of the present invention is to provide a highly effective method for treatment/remission of cancer, and prevention of recurrence/metastasis of cancer at low cost and with few side effects.

Solution to Problem

The present inventors conducted intensive studies with a view to solving the above problem. As a result, they found that oral administration/intake of a medicine and a food/drink containing a urinary alkalinization agent as an active ingredient enables treatment/remission and prevention of ecurrence/metastasis of cancer in patients. They also found that a urinary alkalinization agent can be effectively administered to a patient by transdermal administration of the urinary alkalinization agent, for example, by allowing the patient to take a bath in hot water containing a urinary alkalinization agent, thereby enabling treatment/remission and prevention of recurrence/metastasis of cancer in patients. The present invention was attained based on these findings.

More specifically, the present invention includes the following inventions.

[1] A composition containing a urinary alkalinization agent, for use in treatment or remission of cancer, or prevention of recurrence or metastasis of cancer.

[2] The composition according to [1], in which the urinary alkalinization agent contains one or two or more substances selected from the group consisting of carbonic acid, bicarbonic acid, citric acid, acetic acid, lactic acid, succinic acid, malic acid, silicic acid, an oxide, a hydroxide and salts of them.

[3] The composition according to [1] or [2], for oral administration.

[4] The composition according to [3], being a pharmaceutical composition or a food/drink composition.

[5] The composition according to [3] or [4], containing sodium hydrogen carbonate, magnesium oxide, or citric acid or a salt thereof, as the urinary alkalinization agent.

[6] The composition according to [1] or [2], for transdermal administration.

[7] The composition according to [6], being a bath additive.

[8] The composition according to [7], containing sodium hydrogen carbonate.

[8A] The composition according to any one of [1] to [8], used in combination with an anti-cancer agent.

[8B] The composition according to [8A], in which the anti-cancer agent is an anti PD-1 antibody or lentinan.

[9] A urinary alkalinization agent for use in a method for treatment or remission of cancer, or prevention of recurrence or metastasis of cancer.

[10] The urinary alkalinization agent according to [9], containing one or two or more substances selected from the group consisting of carbonic acid, bicarbonic acid, citric acid, acetic acid, lactic acid, succinic acid, malic acid, silicic acid, an oxide, a hydroxide and salts of them.

[11] The urinary alkalinization agent according to [9] or [10], for oral administration.

[12] The urinary alkalinization agent according to [11], being a pharmaceutical composition or a food/drink composition.

[13] The urinary alkalinization agent according to [11] or [12], containing sodium hydrogen carbonate, magnesium oxide, or citric acid or a salt thereof.

[14] The urinary alkalinization agent according to [9] or [10], for transdermal administration.

[15] The urinary alkalinization agent according to [14], being a bath additive.

[16] The urinary alkalinization agent according to [15] containing sodium hydrogen carbonate.

[16A] The urinary alkalinization agent according to any one of [9] to [16], used in combination with an anti-cancer agent.

[16B] The urinary alkalinization agent according to [16A], in which the anti-cancer agent is an anti PD-1 antibody or lentinan.

[17] Use of a urinary alkalinization agent in producing a medicine used in a method for treatment or remission of cancer, or prevention of recurrence or metastasis of cancer.

[18] The use according to [17], in which the urinary alkalinization agent contains one or two or more substances selected from the group consisting of carbonic acid, bicarbonic acid, citric acid, acetic acid, lactic acid, succinic acid, malic acid, silicic acid, an oxide, a hydroxide and salts of them.

[19] The use according to [17] or [18], in which the medicine is for oral administration.

[20] The use according to [19], in which the urinary alkalinization agent contains sodium hydrogen carbonate, magnesium oxide, or citric acid or a salt thereof.

[21] The use according to [17] or [18], in which the medicine is for transdermal administration.

[22] The use according to [21], in which the medicine has form of a bath additive.

[23] The use according to [22], in which the urinary alkalinization agent contains sodium hydrogen carbonate.

[23A] The use according to any one of [17] to [23], in which the medicine is used in combination with an anti-cancer agent.

[23B] The use according to [23A], in which the anti-cancer agent is an anti PD-1 antibody or lentinan.

[24] A method for treatment or remission of cancer, or prevention of recurrence or metastasis of cancer, comprising administering a urinary alkalinization agent to a cancer patient.

[25] The method according to [24], in which the urinary alkalinization agent contains one or two or more substances selected from the group consisting of carbonic acid, bicarbonic acid, citric acid, acetic acid, lactic acid, succinic acid, malic acid, silicic acid, an oxide, a hydroxide and salts of them,

[26] The method according to [24] or [25], in which the composition is orally administered.

[27] The method according to [26], in which the urinary alkalinization agent contains sodium hydrogen carbonate, magnesium oxide, or citric acid or a salt thereof.

[28] The method according to [24] or [25], in which the composition is transdermally administered.

[29] The method according to [28], in which the composition is administered by taking a bath dissolving the composition.

[30] The method according to [28] or [29], in which the urinary alkalinization agent contains sodium hydrogen carbonate.

[30A] The method according to any one of [24] to [30], in which the composition is used in combination with an anti-cancer agent.

[30B] The method according to [30A], in which the anti-cancer agent is an anti PD-1 antibody or lentinan.

Advantageous Effects of Invention

According to the present invention, it is possible to provide a highly effective method for treatment/remission of cancer, and prevention of recurrence/metastasis of cancer at low cost with few side effects.

BRIEF DESCRIPTION OF DRAWINGS

FIG. 15-1 includes graphs showing evaluation results of the antitumor effect and toxicity in the cases where a urinary alkalinization agent (sodium hydrogen carbonate+magnesium oxide (3:1)), a cancer immunotherapeutic agent (anti-mouse PD-1 antibody) or a urinary alkalinization agent+cancer immunotherapeutic agent was administered to tumor-bearing mice obtained by subcutaneously transplanting B16 mouse melanoma cells. The white square: control group; black square: a urinary alkalinization agent administration group; white circle: cancer immunotherapeutic agent administration group; and black circle: urinary alkalinization agent+cancer immunotherapeutic agent administration group. (A) shows changes of tumor volumes of individual administration groups during a test period as a relative tumor volume (%) to the tumor volume on Day 1 after cell transplantation *: $P<0.05$ vs. control group; ***: $P<0.001$ vs. control group. #: $P<0.05$ vs. urinary alkalinization agent administration group; ###: $P<0.001$ vs. urinary alkalinization agent administration group. $: $P<0.05$ vs. cancer immunotherapeutic agent administration group. (B) shows changes of body weights of individual administration groups during the test period as a relative value based on the body weight (100%) on Day 1 after cell transplantation.

FIG. 15-2 includes graphs showing evaluation results on a change of urine pH value, and the correlation between urine pH value and tumor volume in the cases where a urinary alkalinization agent (sodium hydrogen carbonate+ magnesium oxide (3:1)), a cancer immunotherapeutic agent (anti-mouse PD-1 antibody), or a urinary alkalinization agent+cancer immunotherapeutic agent was administered to tumor-bearing mice obtained by subcutaneously transplanting B16 mouse melanoma cells. The white square: control group; black square: a urinary alkalinization agent administration group; white circle: cancer immunotherapeutic agent administration group; and black circle: urinary alkalinization agent+cancer immunotherapeutic agent administration group. (C) shows changes of pH values of individual administration groups during a test period; and (D) shows the correlation between urine pH value and tumor volume at the final day of the test (Day 15 after the cell transplantation) in the urinary alkalinization agent administration group and the urinary alkalinization agent+cancer immunotherapeutic agent administration group.

DESCRIPTION OF EMBODIMENTS

Figure 1:
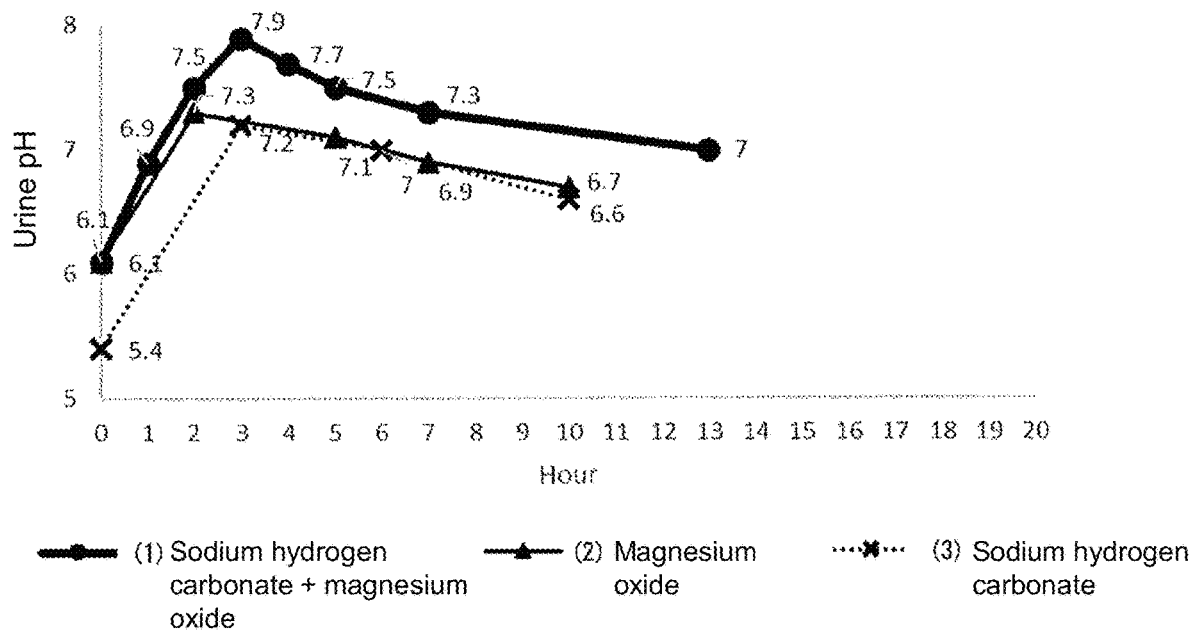
FIG. 1 is a graph showing the urine pH value measured with time after (1) sodium hydrogen carbonate+magnesium oxide, (2) magnesium oxide, and (3) sodium hydrogen carbonate were separately administered to a healthy man (68 years old).

The present invention relates to a composition (hereinafter referred to as "the composition of the present invention") containing a urinary alkalinization agent, for use in treatment or remission of cancer, or prevention of recurrence or metastasis of cancer.

In the present invention, the "urinary alkalinization agent" refers to an agent having an action to alkalinize pHe of cancer cells of a target cancer patient. Whether a compound has the action or not can be determined based on the pH value of urine of a subject administered with or taking the compound. If the urine pH value of a subject administered with the compound shifts towards the alkaline range compared to the pH value before administration or intake of the compound and/or is maintained in the alkaline range, the compound administered or taken is determined to have the action. The determination can be made by measuring the pH value of the urine sampled after initiation of administration or intake or after continuous administration or intake. In the present invention, the "alkalinization of urine" means that the pH value of urine shifts toward the alkaline range compared to the pH value before administration or intake of a compound and/or the pH value is maintained in the alkaline range; preferably means that the urine pH value is 7 or more or beyond 7, further preferably 7.5 or more, and further more preferably 8 or more. In the present invention, the phrase "maintained in the alkaline range" means that the pH value is maintained in the alkaline range for at least one hour, 3 hours, 6 hours, 12 hours, 18 hours or 24 hours or more.

As the "urinary alkalinization agent" available in the present invention, a compound generating hydrogen carbonate ions ($HCO_3^-$) in vivo and a compound having an antacid action (e.g., neutralization of an acid) are mentioned. Examples of compounds having such action include, but are not limited to, carbonic acid, hydrogen carbonate, citric acid, acetic acid, lactic acid, succinic acid, malic acid, silicic acid, an oxide, a hydroxide and salts of these. Examples of the salts include alkali metal salts (e.g., sodium salt, potassium salt), alkaline earth metal salts (e.g., calcium salt), magnesium salts, aluminum salts and combinations of these.

Specific examples of the "urinary alkalinization agent" available in the present invention include sodium hydrogen carbonate (sodium bicarbonate), sodium carbonate, calcium carbonate, magnesium carbonate, citric acid, sodium citrate, potassium citrate, sodium acetate, sodium succinate, sodium malate, sodium lactate, potassium lactate, magnesium oxide, magnesium hydroxide, aluminum hydroxide and aluminum silicate. Preferable examples thereof include sodium hydrogen carbonate, magnesium oxide, citric acid, sodium citrate and potassium citrate. Note that, "sodium hydrogen carbonate" will be sometimes referred to as "sodium bicarbonate" herein and both terms will be interchangeably used.

The composition of the present invention may contain a single or a plurality of urinary alkalinization agents selected from the aforementioned examples.

The urinary alkalinization agent may be industrially synthesized in accordance with a method known in the art or a commercially available product sold as a food or a pharmaceutical product may be used. Alternatively, the urinary alkalinization agent may be derived from a natural product. The urinary alkalinization agent, if it is derived from a natural product, may take form of juice or an extract of the natural product, or a mixture of these; or a concentrate or a dried product of these. Examples thereof include extracts from fruits rich in citric acid (for example, plum, lemon, grapefruit, strawberry, pineapple, kiwi and acerola, preferably plum).

To the composition of the present invention, a urinary alkalinization agent can be added in an amount selected from the range of 0.001 to 99 wt %, preferably 0.001 to 90 wt %, more preferably 0.001 to 80 wt % and further preferably 0.001 to 70 wt %. The amount is not particularly limited and can be appropriately determined depending on the form and use of the composition.

The composition of the present invention may be prepared as a pharmaceutical composition or a food/drink composition having a suitable form for oral administration or oral intake.

Examples of the dosage form of a pharmaceutical composition suitable for oral administration include liquid preparations such as a liquid and a syrup suspension; tablets, pills, capsules, granules and powders (but not limited to these). The liquid preparations may include a liquid preparation prepared at the time of administration by dissolving a preparation with water or the like up to an appropriate concentration. The preparation having a solid dosage form can be coated as needed (for example, sugar coated tablets, gelatin encapsulated tablets, enteric coated tablets). Examples of the dosage forms of foods and drinks suitable for oral intake include beverages such as soft drinks and tea beverages; biscuits, cookies, jellies, candies, confectioneries, tablets, chewable tablets, dusting powders, powders, capsules, granules and health drinks (but not limited to these). In the foods and drinks, in addition to general foods and drinks, health foods (specified health foods (including food for specified health use), nutritional functional food, foods with functional claims, healthy food) are included.

When the composition of the present invention contains a plurality of urinary alkalinization agents, the agents may be contained in a single composition according to the present invention (for example, a combination preparation) or the agents may be individually and separately prepared, placed in a single package suitable for combined administration/intake, wrapped and distributed (for example, a kit preparation). For example, if the composition of the present invention is a combination preparation containing magnesium oxide and sodium hydrogen carbonate, the amount ratio (weight base) of the components in the preparation can be specified as follows: magnesium oxide:sodium hydrogen carbonate=1:1 to 10, preferably 1:2 to 8, and more preferably 1:3.

In the present invention, a commercially available pharmaceutical composition or food/drink composition containing a urinary alkalinization agent as mentioned above and used for a different purpose of use (for example, acid suppressants, laxatives) can be also applied to the use of the present invention. As long as it is applied to the use of the present invention, such a commercially available pharmaceutical composition or food/drink composition is included in the composition of the present invention.

The composition of the present invention may have dosage forms and shapes suitable for transdermal administration.

Examples of the dosage forms and shapes suitable for transdermal administration include solid preparations for external use, liquid preparations for external use (liniment agent, lotion), spray agents (aerosol, pump spray), ointments, creams, gels, patches (tape agents, cataplasms) and bath additives (but not limited to these). The bath additives may have forms ordinarily employed, such liquids, powders, granules and tablets. A bath additive can be used by dissolving it in hot water in a bathtub in taking a bath.

The composition of the present invention may further contain e.g., an excipient, a binder, a disintegrant and a lubricant ordinarily used in production of medicines, food and drinks, external preparations for skin and, bath additives, in addition to a urinary alkalinization agent as mentioned above. These additives can be appropriately selected depending on the desired dosage form and shape and put in use.

Examples of the excipient include water, a sugar (a monosaccharide, a disaccharide, a polysaccharide such as cyclodextrin and alginic acid), a metal salt, kaolin, silicic acid, polyethylene glycol and a mixture of these.

Examples of the binder include simple syrup, a glucose solution, a starch solution, a gelatin solution, polyvinyl alcohol, polyvinyl ether, polyvinyl pyrrolidone, carboxymethyl cellulose, shellac, methyl cellulose, ethyl cellulose and a mixture of these.

Examples of the disintegrant include dried starch, sodium alginate, agar powder, laminaran powder, sodium hydrogen carbonate, calcium carbonate, polyoxyethylene sorbitan fatty acid ester, sodium lauryl sulfate, stearic acid monoglyceride, starch, lactose and a mixture of these.

Examples of the lubricant include purified talc, stearates, borax, polyethylene glycol and a mixture of these.

If necessary, additives ordinarily used for production of, e.g. medicines, foods and drinks, external preparations for skin, and bath additive, such as a diluent, a stabilizer, an isotonic agent, a pH adjuster, a buffer, a solubilizer, a suspending agent, a colorant, a taste-masking agent, an odor-masking agent, a coating agent, a preservative, an antiseptic agent, an anti-oxidizing agent, a sweetener, a seasoning agent, an acidulant and a flavoring agent, can be further appropriately contained.

The composition of the present invention can be used for treatment or remission of cancer or prevention of recurrence or metastasis of cancer. In other words, the present invention relates to a method for treatment or remission of cancer, or prevention of recurrence or metastasis of cancer, including administering or feeding the composition of the present invention to a cancer patient.

In the present invention, the "treatment or remission of cancer" means not only the state where cancer completely disappears but also the state where cancer temporarily or permanently shrinks or disappears as well as the state where cancer stops growing (exacerbation) and remains in stable condition. The term "treatment or remission of cancer" of the present invention includes one or more of state observed in cancer patients, such as a reduction in size of cancer tumor, a reduction in level of a cancer-marker(s), improvement of symptom associated with cancer, extension of the overall survival period, extension of progression-free survival period and extension of median survival period, compared to before administration or intake of the composition of the present invention.

In the present invention, the "preventing recurrence or metastasis of cancer" refers to reducing a risk of re-emergence or starting growth (exacerbation) of cancer once treated or attained remission or reducing a risk of migration of cancer cells to a site (organ) different from a primary lesion and starting growth. The term "preventing recurrence or metastasis of cancer" of the present invention includes one or more of state, such as extension of a disease-free survival period, a progression-free survival period and a relapse-free survival period, and improvement of a disease-free survival rate, compared to the case where the composition of the present invention is not administered or taken.

In the present invention, examples of the "cancer" include, but are not limited to, blood cancers (e.g., acute myeloid leukemia, chronic myeloid leukemia, malignant lymphoma and multiple myeloma), solid cancers (brain tumor/glioma, pituitary adenoma, acoustic schwannoma, malignant uveal melanoma, meningioma, pharyngeal cancer, laryngeal cancer, tongue cancer, thyroid cancer, breast cancer, lung cancer, thymoma, thymic cancer, mesothelioma, esophageal cancer, gastric cancer, colorectal cancer, hepatocellular carcinoma, bile duct cancer, pancreatic cancer, renal cell carcinoma, bladder cancer, prostate cancer, renal pelvis/ureteral cancer, penis cancer, testis (testicle) tumor, uterine cancer, ovarian cancer, vulvar cancer, skin cancer, malignant melanoma (skin), basal cell carcinoma, skin cancer prodrome, intraepidermal cancer, squamous cell carcinoma, mycosis fungoides, malignant bone tumor (osteosarcoma), soft tissue sarcoma, chondrosarcoma, malignant fibrous tissue pitch) and metastatic cancers of these.

The dose or the amount of intake of the composition of the present invention, which varies depending on factors such as the type and severity of cancer, the age, body weight and conditions of a patient and the dosage form and administration route of the composition of the present invention, is preferably an amount sufficient to shift the pH value of urine of a patient administered or fed with the composition, toward the alkali pH range and/or to maintain alkalinization, more preferably, 7 or more or beyond 7, further preferably 7.5 or more, and further more preferably 8 or more.

If the composition of the present invention has a dosage form suitable for oral administration or oral intake, a composition, which contains a urinary alkalinization agent in a dose selected from 1 to 20 g, preferably 1 to 10 g, and further preferably 1 to 5 g, is orally administered or taken every day, every other day or at the intervals of several days (the dose being divided into 1 to 5 portions per day (for example, 2 or 3)). If the composition of the present invention contains a plurality of urinary alkalinization agents, the amount of the urinary alkalinization agent may be specified as the amount of individual urine alkalinization agents, and the amounts of the individual alkalinization agents can be separately selected.

If the composition of the present invention has a dosage form suitable for transdermal administration, in particular, the form of a bath additive, a composition, which contains a urinary alkalinization agent in an amount selected from 0.1 g to 1 g, preferably 0.2 g to 0.75 g, further preferably 0.25 g to 0.5 g and 0.05 to 5 g per liter, is dissolved in a hot water in a tub, and then, the user is allowed to sit in the bathtub for about 5 to 30 minutes, preferably about 10 to 20 minutes, every day, every other day or at the interval of several days. In this manner, the composition can be transdermally administered. The temperature of the hot water, although it is not particularly limited, can be selected from the temperature range suitable for bathing and may fall within the range of about 38° C. to 42° C.

To describe more specifically, the urinary alkalinization agent, if it is magnesium oxide, can be orally administered or fed in a dose selected from 1 to 5 g and preferably 1 to 2 g every day, every other day or at the intervals of several days (the dose being divided into 1 to 5 portions per day). The urinary alkalinization agent, if it is sodium hydrogen carbonate, can be orally administered or fed in a dose selected from 1 to 15 g, and preferably 1 to 10 g every day, every other day or at the intervals of several days (the dose being divided into 1 to 5 portions per day). If the urinary alkalinization agent is citric acid and provided in the dosage form of a plum extract (for example, "Ume-terpene", manufactured by NAKANO. B.C. Co., Ltd.), a plum extract containing at least 1 g of citric acid can be orally taken in a dose selected from 15 g to 45 g, and preferably 15 g to 30 g every day, every other day or at the intervals of several days (the dose being divided into 1 or 2 portions per day). The urinary alkalinization agent, if it is sodium hydrogen carbonate and provided in the form of a bath additive, can be transdermally administered to a user by dissolving it in an amount selected from 40 to 200 g and preferably 40 to 100 g in 150 to 200 liters of hot water (37 to 42° C.), and allowing the user to sit in the bathtub for about 10 to 20 minutes, one to 3 times per day.

A plurality of methods selected from the aforementioned oral administration, oral intake and transdermal administration methods may be used in combination.

The composition of the present invention can be used in combination with an anti-cancer agent.

In the present invention, the phrase "used in combination" means that the composition of the present invention and an anti-cancer agent are simultaneously used (administered). Other than the simultaneous administration, sequential administration, in which the composition and an anti-cancer agent are successively administered at the respectively determined intervals over the treatment period, is included. The administration routes and means for the components to be used in combination may be the same or different.

As the anti-cancer agent to be used in combination with the composition of the present invention, an existing anti-cancer agent, molecularly targeted drug for cancer and a cancer immunotherapeutic agent used in the method for treatment or remission of cancer can be mentioned. Examples thereof include, but are not limited to, tegafur, tegafur/uracil combination drug, tegafur/gimeracil/oteracil potassium combination drug (trade name: TS-1 (registered trademark)), fluorouracil, gemcitabine (trade name: Gemzar (registered trademark)), enocitabine, carmofur, doxyfluridine, cytarabine, cytarabine ocfosphate, mercaptopurine, fludarabine, capecitabine, methotrexate, cladribine, pemetrexed (trade name: ALIMTA (registered trademark)), hydroxycarbamide, cyclophosphamide, thiotepa, ifosfamide, busulfan, dacarbazine, melphalan, ranimustine, nimustine, temozolomide, carboplatin, cisplatin, oxaliplatin (trade name: Elplat (registered trademark)), nedaplatin, doxorubicin, aclarubicin, idarubicin, actinomycin D, daunorubicin, zinostatin stimalamer, bleomycin, mitomycin C, pirarubicin, epirubicin, peplomycin, amrubicin, vinca alkaloids, taxane, a topoisomerase inhibitor, sorafenib, erlotinib, axitinib, everolimus, sunitinib, imatinib, lapatinib, rituximab, dasatinib, bortezomib, tamibarotene, gefitinib, ibritumomab, nilotinib, temsirolimus, trastuzumab, panitumumab, tretinoin, gemtuzumab ozogamicin, crizotinib, afatinib, bevacizumab (trade name: Avastin (registered trademark)), paclitaxel (trade name: ABRAXANE (registered trademark)), docetaxel (trade name: Taxotere (registered trademark)), nivolumab (trade name: Opdivo (registered trademark)), lentinan, pembrolizumab (trade name: KEYTRUDA (registered trademark)), ipilimumab (trade name: YERVOY (registered trademark)), atezolizumab (trade name: TECENTRIQ (registered trademark)), and (2S)-2-[(2S,3R)-3-amino-2-hydroxy-4-phenylbutanoylamino]-4-methylpentanoic acid (common name: Ubenimex) (trade name: Bestatin (registered trademark)).

An anti-cancer agent can be used at a dose and schedule sufficient to maintain the immune function of the patient administered with the agent or so as not to significantly reduce the immune function (at a rate of, for example, 40% or more, 50% or more, 60% or more, 70% or more). A change in immune function of a patient can be determined based on variation of one or more values of neutrophil count, granulocyte count, monocyte count, lymphocyte count and platelet count in the peripheral blood, and preferably, based on a variation of lymphocyte count.

An anti-cancer agent can be administered in a dose, which corresponds to 90%, 80%, 70%, 60%, 50%, 40% or less to the dose of the anti-cancer agent alone and/or administered for a shorter dosing period and/or at a schedule having a longer drug holiday compared to those when the anti-cancer agent alone is administered. In this manner, incidence of side effects (examples thereof include, but not limited to, bone marrow suppression, hemolytic anemia, disseminated intravascular coagulation, fulminant hepatitis, dehydration, enteritis, interstitial pneumonia, stomatitis, gastrointestinal ulcer, gastrointestinal bleeding, gastrointestinal perforation, acute renal failure, mucocutaneous eye syndrome, toxic epidermal necrosis, psychiatric neuropathy, acute pancreatitis, rhabdomyolysis and olfactory anesthesia) caused by administration of an anti-cancer agent can be suppressed or delayed.

According to the present invention, it is possible to inhibit or suppress a single or a plurality of mechanisms involved in malignant alteration, proliferation and metastasis of cancer, such as malignant transformation of cells, proliferation of cells, expression of a cancer gene, activation of growth factor, acceleration of glycolysis, acceleration of DNA synthesis, acceleration of the cell cycle, downregulation of apoptosis induction, cell migration, angiogenesis, cancer metastasis and drug resistance, in the patient to which the composition of the present invention is administered or fed. Owing to the inhibition or suppression, activity of cancer can be reduced for treatment or remission, or prevention of recurrence/metastasis thereof. Particularly, in intractable (progressive and/or end-stage) cancer, the effect of the composition is remarkable and the survival rate (median survival) from the cancer patient can be greatly enhanced.

The composition of the present invention alone is effective for treatment or remission of cancer, or prevention of recurrence or metastasis of cancer; however, if the composition is used in combination with an anti-cancer agent, economic burden of cancer patients and burden of the medical insurance finances of the country and local governments can be greatly reduced. An immune checkpoint inhibitor, nivolumab (trade name: Opdivo) recently developed is an epoch-making anti-cancer agent; however, production cost is high, and the drug price is extremely high. Because of this, economic burden of cancer patient is high and has become a social problem. However, if the anti-cancer agent is used in combination with the composition of the present invention, the dose of anticancer drug can be reduced to decrease economic burden of cancer patients.

EXAMPLES

Now, the present invention will be more specifically described by way of Examples, below; however, the present invention is not limited by these examples.

[Example 1] Change of Urine pH by Intake of Urinary Alkalinization Agent (I)

After a healthy man (68 years old) was allowed to take a urinary alkalinization agent in accordance with the following dose and schedule, a change of urine pH value was measured with time.

(Dose/Schedule)

(1) 3 g of sodium hydrogen carbonate (manufactured by Kenei Pharmaceutical Co., Ltd.) was allowed to take before a meal once a day and 1 g of magnesium oxide (manufactured by Kenei Pharmaceutical Co., Ltd.) was allowed to take after a meal once a day;

(2) Three tablets (1 g) of magnesium oxide (manufactured by Kenei Pharmaceutical Co., Ltd.) were allowed to take after a meal once a day;

(3) 3 g of sodium hydrogen carbonate (manufactured by Kenei Pharmaceutical Co., Ltd.) was allowed to take before a meal once a day.

(Results)

The measurement results of urine pH values after administration of the individual urinary alkalinization agents are shown in FIG. 1. In any one of the oral administration cases of the urinary alkalinization agents, alkalinization of urine pH value was confirmed. Particularly, in the combined administration (1) of sodium hydrogen carbonate and magnesium oxide, urine pH value increased up to 7.9, which shows that the urinary alkalinization action thereof is higher than others. At the same time, the urine pH value thereof was long maintained in the alkaline pH range (pH7 or more) compared to the urine pH values provided by the urinary alkalinization agents (2) and (3).

[Example 2] Change of Urine pH by Intake of Urinary Alkalinization Agent (II)

After a healthy man (68 years old) was allowed to take a urinary alkalinization agent in accordance with the following dose and schedule, urine pH value was measured.

(Dose/Schedule)

(1) one packet of a fine-grain gastrointestinal medicine ("Panciron G", manufactured by ROHTO Pharmaceutical Co., Ltd.), which contains sodium hydrogen carbonate (650 mg), heavy magnesium carbonate (200 mg) and precipitated calcium carbonate (100 mg) as an acid suppressor, was allowed to take after a meal twice a day at an interval of 5 hours;

(2) Three tablets (1 g in total) of magnesium oxide (manufactured by Kenei Pharmaceutical Co., Ltd.) were allowed to take after a meal once a day;

(3) Three tablets (1 g in total) of magnesium oxide (manufactured by Kenei Pharmaceutical Co., Ltd.) were allowed to take after a meal once a day; at the same time, one packet of a fine-grain gastrointestinal medicine ("Panciron G", manufactured by ROHTO Pharmaceutical Co., Ltd.), which contains sodium hydrogen carbonate (650 mg), heavy magnesium carbonate (200 mg) and precipitated calcium carbonate (100 mg) as an acid suppressor, was allowed to take after a meal twice a day at an interval of 5 hours.

(Results)

Figure 2:
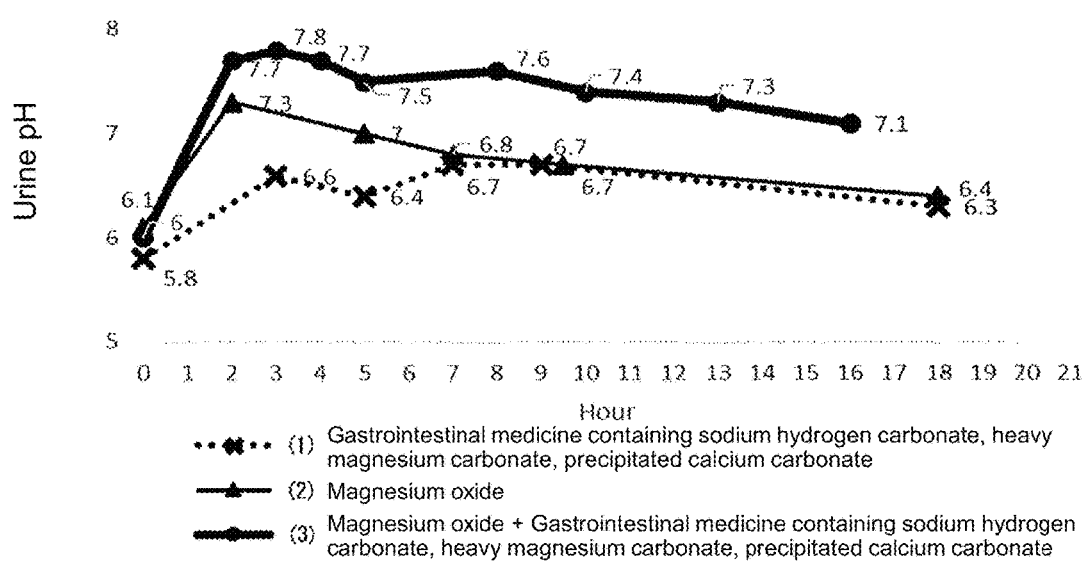
FIG. 2 is a graph showing the urine pH value measured with time after (1) a gastrointestinal medicine containing sodium hydrogen carbonate, heavy magnesium carbonate and precipitated calcium carbonate, (2) magnesium oxide and (3) magnesium oxide+a gastrointestinal medicine containing sodium hydrogen carbonate, heavy magnesium carbonate and precipitated calcium carbonate were separately administered to a healthy man (68 years old).

The measurement results of urine pH values after administration of the individual urinary alkalinization agents are shown in FIG. 2.

In any one of the oral administration cases of the urinary alkalinization agents, alkalinization of urine pH value was confirmed. Particularly, in the combined administration (3) of magnesium oxide and a gastrointestinal medicine containing a urinary alkalinization agent (sodium hydrogen carbonate, heavy magnesium carbonate, precipitated calcium carbonate) as an acid suppressor, urine pH value increased up to 7.8, which shows that the urinary alkalinization action is higher than others. At the same time, urine pH value thereof was long maintained in the alkaline pH range (pH7 or more) compared to the urine pH values provided by the urinary alkalinization agents (1) and (2).

[Example 3] Change of Urine pH by Intake of Urinary Alkalinization Agent (III)

After a healthy man (68 years old) was allowed to take a urinary alkalinization agent in accordance with the following dose and schedule, urine pH value was measured.

(Dose/Schedule)

(1) three tablets (1 g in total) of magnesium oxide (manufactured by Kenei Pharmaceutical Co., Ltd.) were allowed to take after a meal once a day; at the same time, a single packet of a gastrointestinal medicine ("Ohta's Isan <divided powder>", manufactured by Ohta's Isan Co., Ltd.) containing sodium hydrogen carbonate (625 mg), precipitated calcium carbonate (133 mg), magnesium carbonate (26 mg) and synthetic aluminum silicate (273.4 mg) as an acid suppressor, was allowed to take after a meal twice a day at the interval of 5 hours;

(2) three tablets (1 g in total) of magnesium oxide (manufactured by Kenei Pharmaceutical Co., Ltd.) were allowed to take after a meal once a day;

(3) a single packet of a gastrointestinal medicine ("Ohta's Isan <divided powder>", manufactured by Ohta's Isan Co., Ltd.) containing sodium hydrogen carbonate (625 mg), precipitated calcium carbonate (133 mg), magnesium carbonate (26 mg) and synthetic aluminum silicate (273.4 mg) as an acid suppressor was allowed to take after a meal twice a day at the interval of 5 hours.

(Results)

Figure 3:
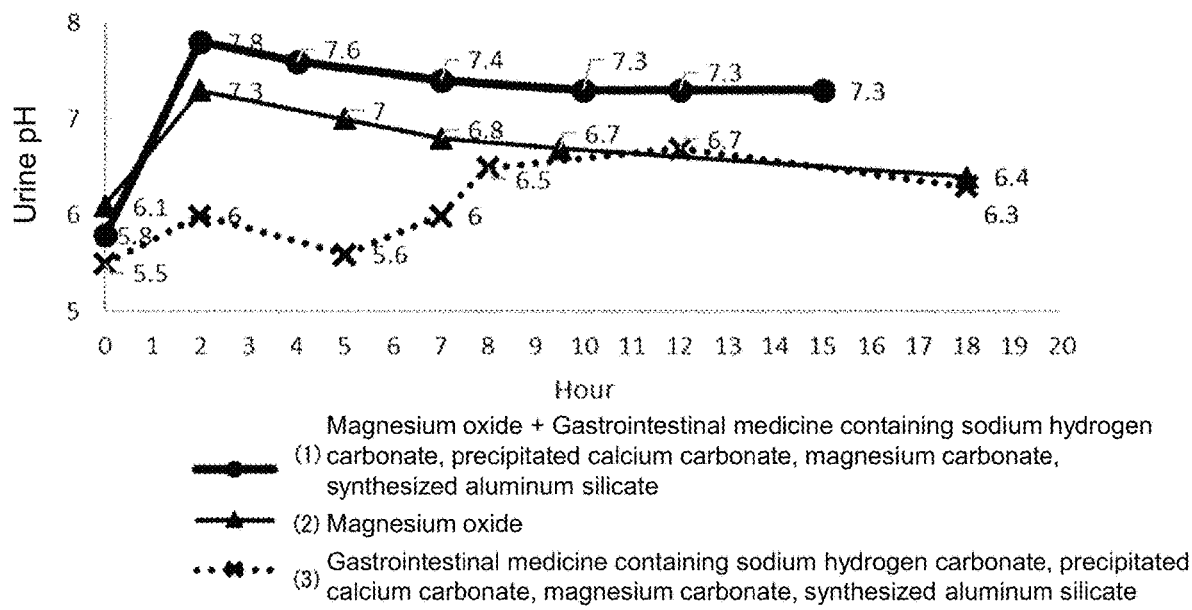
FIG. 3 is a graph showing the urine pH value measured with time after (1) magnesium oxide+a gastrointestinal medicine containing sodium hydrogen carbonate, precipitated calcium carbonate, magnesium carbonate and synthetic aluminum silicate, (2) magnesium oxide and (3) a gastrointestinal medicine containing sodium hydrogen carbonate, precipitated calcium carbonate, magnesium carbonate and synthetic aluminum silicate were separately administered to a healthy man (68 years old).

The measurement results of urine pH values after administration of the individual urinary alkalinization agents are shown in FIG. 3. In any one of the oral administration cases of the urinary alkalinization agents, alkalinization of urine pH value was confirmed. Particularly, in the combined administration (1) of magnesium oxide and a gastrointestinal medicine containing a urinary alkalinization agent (precipitated calcium carbonate, magnesium carbonate, synthetic aluminum silicate) as an acid suppressor, urine pH value increased up to 7.8, which shows that the urinary alkalinization action is higher than others. At the same time, urine pH value thereof was long maintained in the alkaline pH range (pH7 or more) compared to the urine pH values provided by the urinary alkalinization agents (2) and (3).

[Example 4] Change of Urine pH by Intake of Urinary Alkalinization Agent (IV)

After a healthy man (68 years old) was allowed to take a urinary alkalinization agent in accordance with the following dose and schedule, urine pH value was measured.

(Dose/Schedule)

(1) three tablets (1 g in total) of sodium hydrogen carbonate (manufactured by Kenei Pharmaceutical Co., Ltd.) were allowed to take after a meal once a day;

(2) a single pouch (15 g) of a plum extract ("Umeterpene", manufactured by NAKANO. B.C. Co., Ltd.) (plum extract containing 1 g or more of citric acid) was allowed to take before a meal once a day;

(3) three tablets (1 g in total) of sodium hydrogen carbonate (manufactured by Kenei Pharmaceutical Co., Ltd.) were allowed to take after a meal once a day; at the same time, a single pouch (15 g) of a plum extract ("Umeterpene", manufactured by NAKANO. B.C. Co., Ltd.) was allowed to take before a meal once a day.

(Results)

Figure 4:
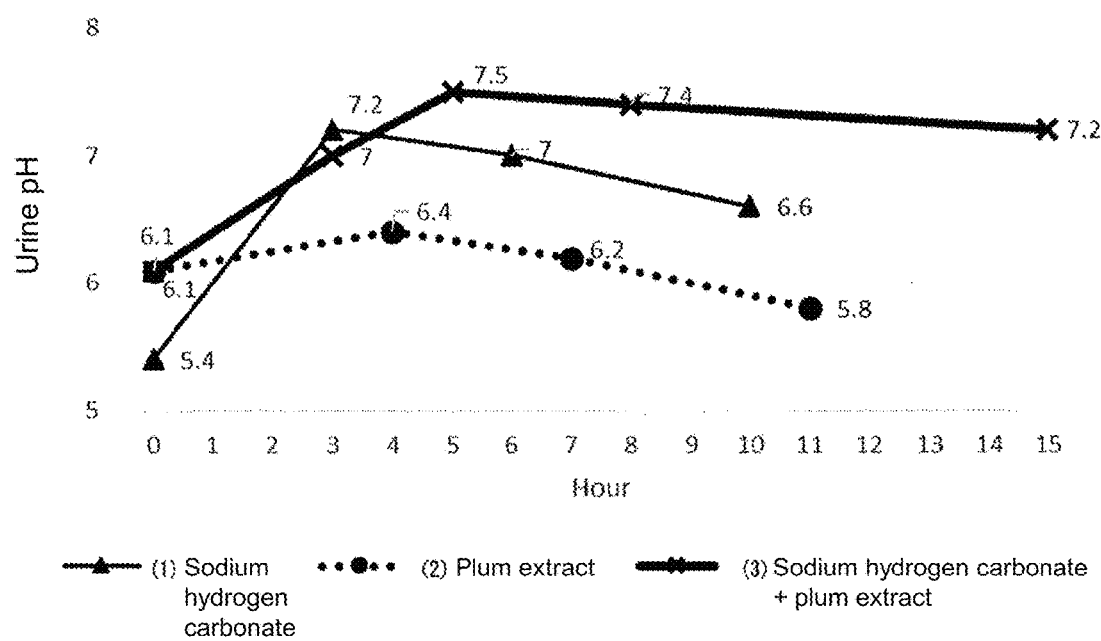
FIG. 4 is a graph showing the urine pH value measured with time after (1) sodium hydrogen carbonate, (2) a plum extract and (3) sodium hydrogen carbonate+a plum extract were separately administered to a healthy man (68 years old).

The measurement results of urine pH values after administration of the individual urinary alkalinization agents are shown in FIG. 4. In any one of the oral administration cases of the urinary alkalinization agents, alkalinization of urine pH value was confirmed. Particularly, in the combined administration (3) of sodium hydrogen carbonate and a plum extract rich in citric acid, urine pH value increased up to 7.5, which shows that the urinary alkalinization action is higher than others. At the same time, urine pH value thereof was long maintained in the alkaline pH range (pH7 or more) compared to the pH values provided by the urinary alkalinization agents (1) and (2).

[Example 5] Change of Urine pH by Transdermal Administration (Getting in a Bath) of Urinary Alkalinization Agent (V)

Figure 5:
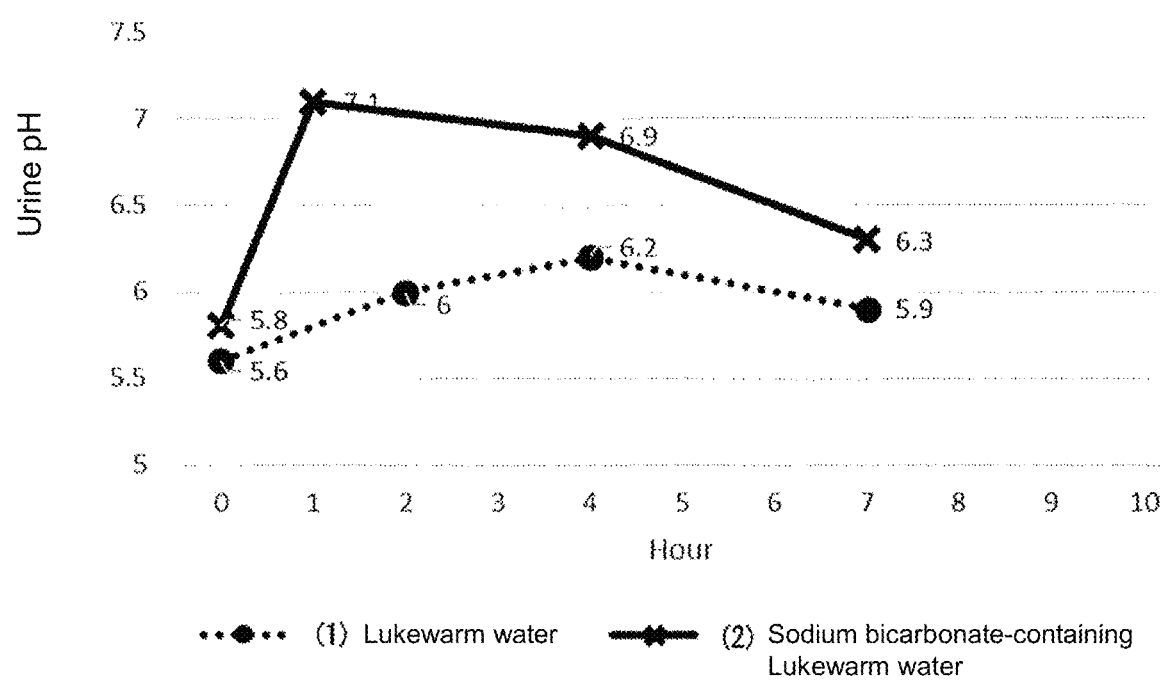
FIG. 5 is a graph showing the urine pH value measured with time after a healthy man (68 years old) was allowed to take (1) a lukewarm bath and (2) a bath containing sodium bicarbonate, separately.

After a healthy man (68 years old) was allowed to take a bath as follows and the urine pH value was measured.
(Dose/Schedule)
(1) getting in a bath of 200 liters of lukewarm water (38° C.) (pH value: 7.0), for about 20 minutes;
(2) getting in a sodium-bicarbonate bath (pH value: 8.3) prepared by dissolving sodium bicarbonate (50 g) in 200 liters of lukewarm water (38° C.), for about 20 minutes.
(Results)
The measurement results of urine pH values after getting in individual bathes are shown in FIG. 5. The urine pH value increased by getting in a sodium bicarbonate bath up to 7.1 (alkalinization), which shows that the urinary pH value is higher than that in lukewarm water. At the same time, urine pH value thereof was long maintained in the alkaline pH range compared to the pH value provided by lukewarm water containing no sodium bicarbonate. As a result, it is suggested that hydrogen carbonate ions from sodium bicarbonate passed through the human skin and entered the blood to alkalinize the urine.

[Example 6] Lung Cancer Patient (Female, 77 Years Old)

A patient (female, 77 years old) successively underwent a surgery for breast cancer in March, 2009, a surgery for endometrial cancer in October, 2010 and a surgery for lung cancer (adenocarcinoma, upper right lobe) in December, 2011.

From January, 2012, application of a urinary alkalinization therapy, including orally administering magnesium oxide (laxative, Magmitt (manufactured by Kyowa Chemical Industry Co., Ltd.)) every day in a dose of 2 g per day after a meal three times (the dose being divided into three portions), was initiated.

Oral administration of magnesium oxide has been continued at present. As a result, recurrence and metastasis of lung cancer have not been observed in the lung cancer patient.

The patient was found to have another cancer and experienced recurrence/metastasis within a year and underwent three treatments (surgeries). The patient was usually determined to have an extremely high risk of developing further another cancer and experiencing recurrence/metastasis. However, the urine pH value thereof has been kept in the alkaline pH range by continuous administration of magnesium oxide. Neither development of another cancer nor recurrence/metastasis has been found up to present.

[Example 7] Gastric Lymphoma Patient (Female, 76 Years Old)

A patient (female, 76 years old) was diagnosed with gastric lymphoma in September, 2015. To the patient, application of a urinary alkalinization therapy including daily oral administration of sodium hydrogen carbonate (6 g/day) and magnesium oxide (2 g/day), was initiated from October, 2015.

Figure 6:
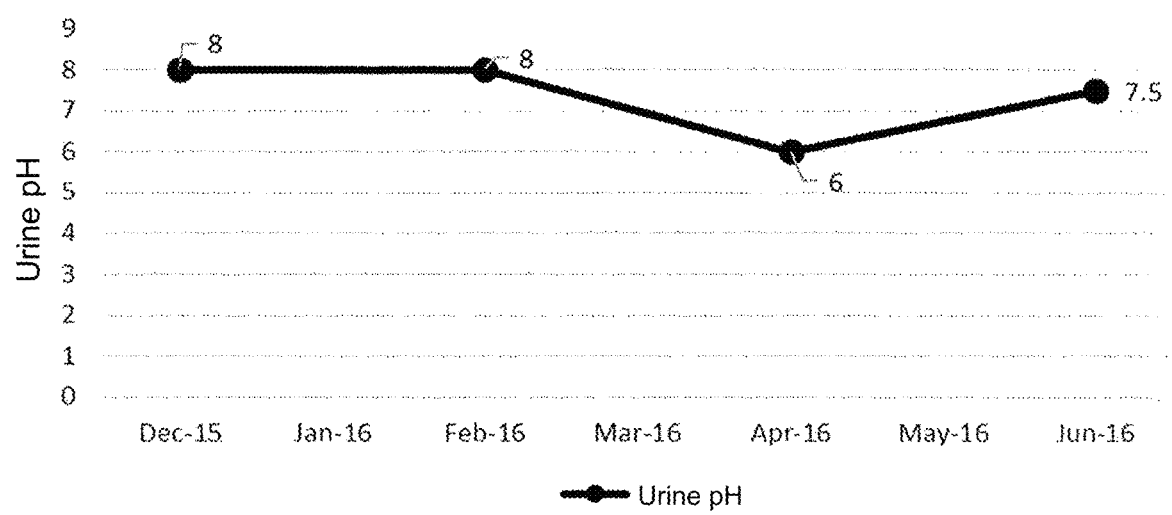
FIG. 6 includes a graph (A) showing the urine pH value measured with time after sodium hydrogen carbonate and magnesium oxide were administered to a patient (76 years old) diagnosed with gastric lymphoma; and photographs showing endoscope images (B) of the stomach before and after administration of sodium hydrogen carbonate and magnesium oxide. The white arrows herein indicate lymphoma (B).
Figure 6:
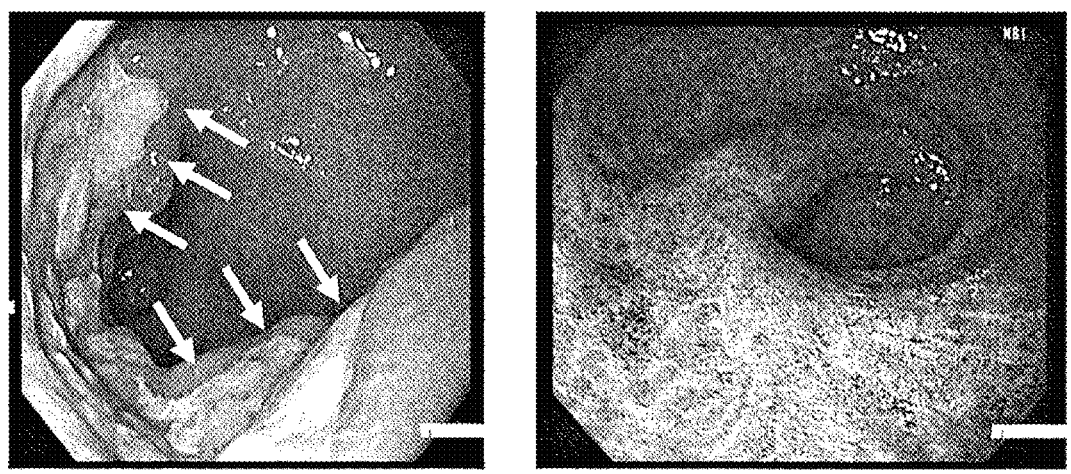

As a result, urine pH value of the patient was long maintained in an alkaline pH range (FIG. 6 (A)). Although none of cancer chemotherapies were applied to the patient, gastric lymphoma completely disappeared in May, 2016 (FIG. 6 (B), right).

Note that, acidification of urine pH value was temporarily observed in around April, 2016. The acidification occurred because the dose of a urinary alkalinization agent was temporarily reduced for patient's personal reason. However, after the dosing was resumed, the pH value was alkalinized again.

[Example 8] Pancreatic Cancer Patient (Male, 74 Years Old) Associated with Cancerous Peritonitis and Liver Metastasis A patient (male, 74 years old) was diagnosed with Stage-IV pancreatic cancer (tail cancer) associated with cancerous peritonitis and liver metastasis in September, 2016.

The patient received a combination chemotherapy with Gemzar and Abraxane each in a general dose from October, 2016, and sequentially, a chemotherapy using TS-1 in a general dose; however, the patient experienced a side effect such as numbness in a limb.

Administration of Abraxane and TS-1 was stopped from November, 2016 and application of a urinary alkalinization therapy including daily oral administration of sodium hydrogen carbonate (6 g/day) and a plum extract containing 1 g or more of citric acid (15 g/day) to the patient while administering Gemzar in a half dose, was initiated from January, 2017.

Figure 7:
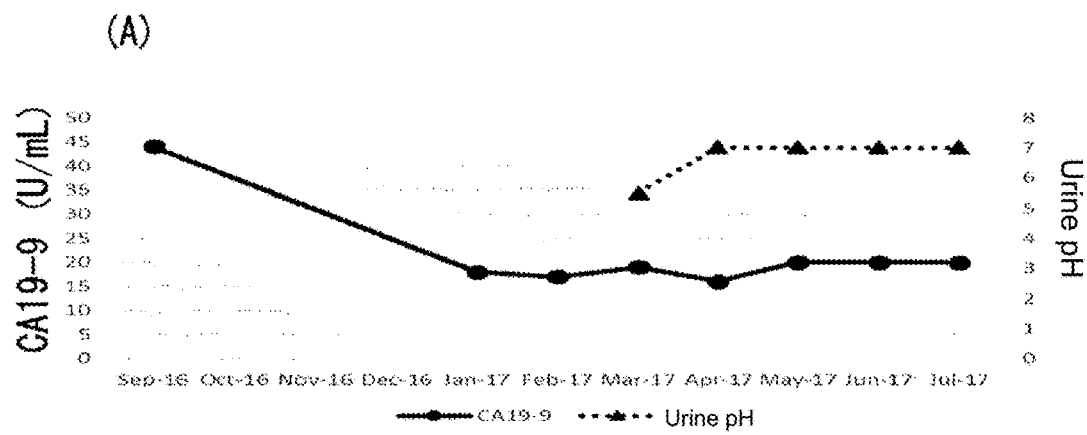
FIG. 7 includes a graph (A) showing the level of a tumor marker (CA19-9) in the blood and the urine pH values measured with time before and after sodium hydrogen carbonate and a plum extract were administered to a male patient (74 years old) diagnosed with pancreatic cancer (tail cancer) associated with cancerous peritonitis and liver metastases; and photographs showing CT images (B) of the liver and pancreas (tail).
Figure 7:
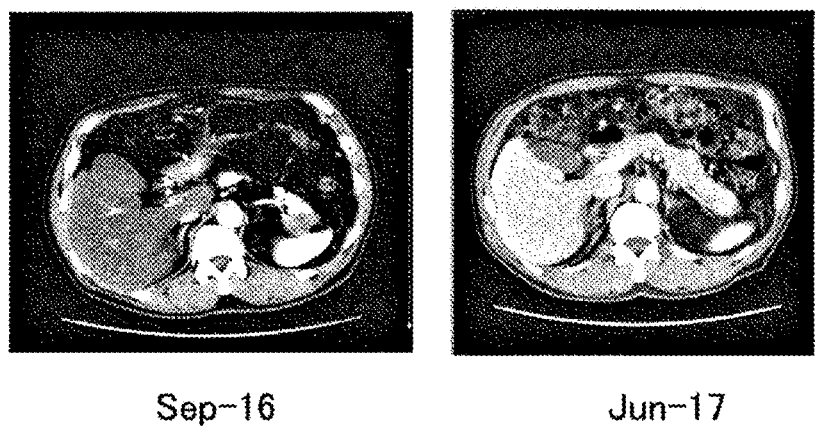

As a result, it was found that a tumor marker (CA19-9) blood level decreased and reached a plateau at a level of around 15 to 20 U/mL in January, 2017; whereas, the urine pH value was alkalinized and maintained at the same value in April, 2017 (FIG. 7 (A)). Also, in the CT image (FIG. 7 (B)), disappearance of liver metastasis and reduction in amount of the ascites were confirmed. The urinary alkalinization therapy has been continued and development of another cancer and recurrence/metastasis have not been confirmed.

The five year survival rate of an end-stage pancreatic cancer patient (70's, male, Stage IV) is reported as about 1.0% even though the rate slightly varies depending on the application or non-application of, e.g., a chemotherapy. The end-stage pancreatic cancer is still an untreatable disease having no effective therapy, at present. Nevertheless, in the patient mentioned above, development of another cancer and recurrence/metastasis have not been confirmed up to present. The result is unpredictable from common technical knowledge on disease condition and survival period of end-stage pancreatic cancer patients and regarded as an extraordinary effect, i.e., a therapeutic effect and remission effect, based on administration of a urinary alkalinization agent according to the present invention.

[Example 9] Recurrent Lung Cancer Patient (Female, 76 Years Old)

A patient (female, 76 years old) was diagnosed with lung cancer (multiple lung cancer) (Stage IIIA (pT1bN2M0)) in November, 2016. On Nov. 29, 2016, the right upper lobe and lower right lobe were partially resected.

From January, 2017, administration of ALIMTA (650 mg) at the intervals of 3 to 4 weeks to the patient, was started simultaneously with a urinary alkalinization therapy including daily oral administration of a gastrointestinal medicine containing sodium hydrogen carbonate (650 mg), heavy magnesium carbonate (200 mg) and precipitated calcium carbonate (100 mg) as an acid suppressant×3 times/day and magnesium oxide (2 g/day).

Figure 8:
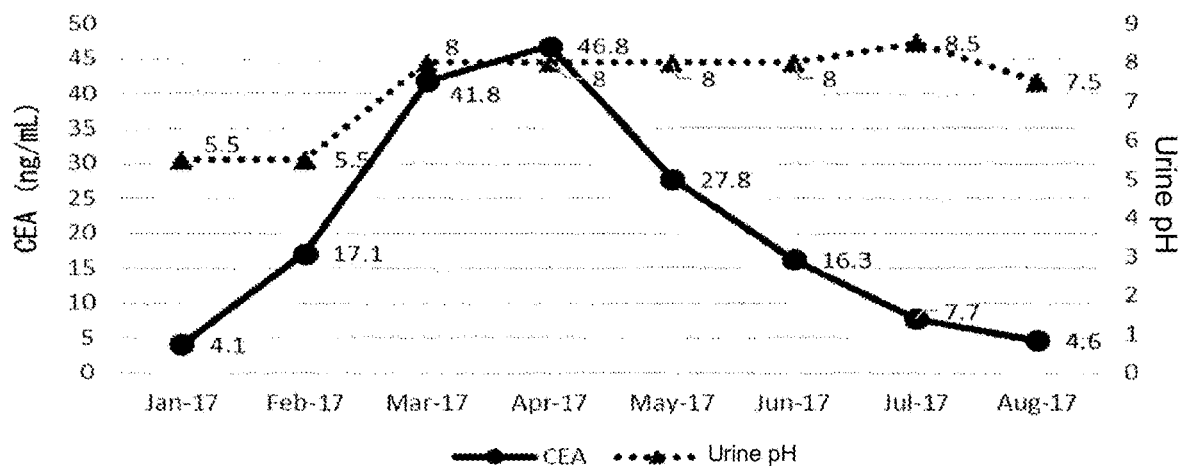
FIG. 8 is a graph showing the level of a tumor marker (CEA) in the blood and the urine pH values measured with time before and after a gastrointestinal medicine containing sodium hydrogen carbonate and magnesium oxide were separately administered to a female patient (76 years old) diagnosed with recurrent lung cancer (multiple lung cancer).

As a result, it was confirmed that the urine pH value was alkalinized and maintained at the same value, and that a tumor marker (CEA) level in the blood decreased from 46.8 ng/mL (April, 2017) up to 4.6 ng/mL (Aug. 17, 2017) (FIG. 8). The urinary alkalinization therapy has been continued and development of another cancer and recurrence/metastasis have not been confirmed.

The five year survival rate of an end-stage lung cancer patient (70's, female, Stage III) is reported as about 22.6% even though the rate slightly varies depending on the application or non-application of, e.g., a chemotherapy. The end-stage lung cancer is still an untreatable disease having no effective therapy, at present. Since no effective therapy is currently present, the end-stage lung cancer is still regarded as an untreatable disease. Nevertheless, in the above patient, development of another cancer and recurrence/metastasis have not been confirmed. The result is unpredictable from common technical knowledge on disease condition and survival period of recurrent lung cancer patients and regarded as an effect, i.e., a therapeutic effect and remission effect, based on administration of a urinary alkalinization agent according to the present invention.

[Example 10] Malignant Lymphoma Patient (Female, 58 Years Old)

A patient (female, 58 years old) was diagnosed with malignant lymphoma at the age of 37 years old (July 1996) and immediately treated with Gemzar, and also transplanted with autologous stem cells in 1997. Thereafter, recurrence (rash in the left thigh) of malignant lymphoma was observed in November, 2014. Thus, administration of Gemzar, a urinary alkalinization treatment including daily oral administration of sodium hydrogen carbonate (6 g/day) and magnesium oxide (2 g/day) to the patient, was initiated from January 2015.

Figure 9:
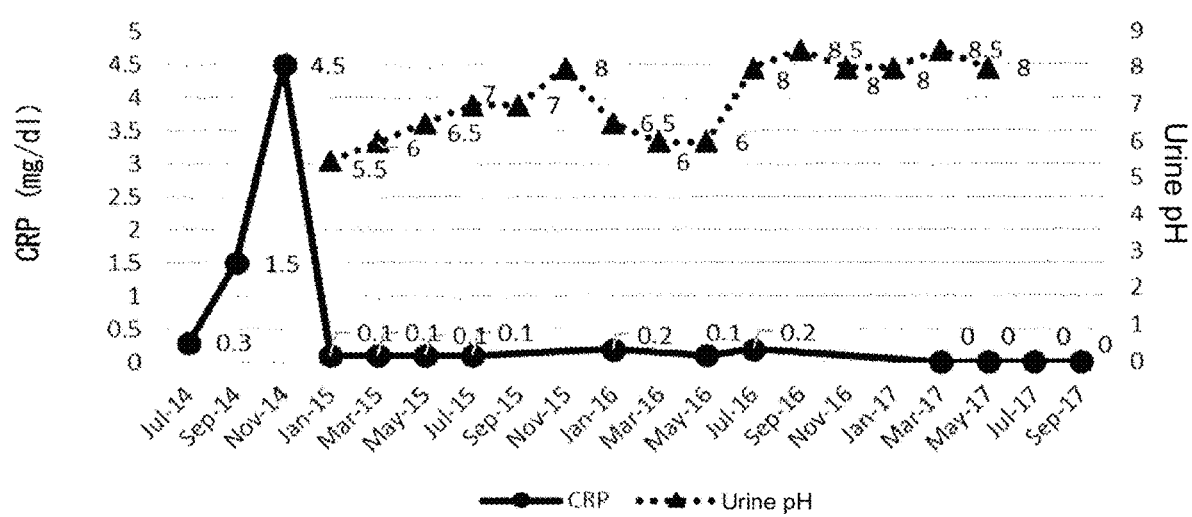
FIG. 9 is a graph showing the level of a tumor marker (CRP) in the blood and the urine pH values measured with time before and after gemcitabine, sodium hydrogen carbonate and magnesium oxide were administered to a female patient (58 years old) diagnosed with malignant lymphoma.

As a result, it was confirmed that the urine pH value was alkalinized, and that an inflammation marker (CRP) level fell within a normal range in January, 2015 (FIG. 9). After that, during the period up to May, 2016, the urinary alkalinization therapy was once interrupted. As a result, acidification of urine and recurrence of malignant lymphoma (rash in the left thigh) were observed. However, gemcitabine was temporarily administered and a urinary alkalinization therapy was continuously applied without fail, with the result that the disease was successfully and completely controlled. Up to present, development of another cancer and recurrence/metastasis have been avoided.

Almost all patients with malignant lymphoma treated by a currently available therapy and then experienced recurrence die within a year; whereas, development of another cancer and recurrence/metastasis of the patient mentioned above have not been confirmed up to present, as described above. The result is unpredictable from common technical knowledge on disease condition and survival period of general recurrent malignant lymphoma patients and regarded as an effect, i.e., a therapeutic effect and remission effect, based on administration of a urinary alkalinization agent according to the present invention.

[Example 11] Breast Cancer Patient (Female, 45 Years Old) Associated with Lung Metastasis A patient (female, 45 years old) was diagnosed with breast cancer at the age of 37 years old and underwent a surgical operation. In January, 2011, transfer of recurrent breast cancer to the lung was found. Administration of Taxotere (80 mg/m$^2$) was continued at the intervals of 3 weeks. However, six months later, the patient experienced a severe side effect. Because of this, the dose of Taxotere was reduced to 60 mg/m$^2$ (intervals of 3 weeks). However, the disease did not become stable. Then, the dose was reduced to 30 mg/m$^2$ (intervals of 4 to 5 weeks) from January, 2012; at the same time, application of a urinary alkalinization therapy including daily oral administration of gastrointestinal medicine containing sodium hydrogen carbonate (650 mg), heavy magnesium carbonate (200 mg), precipitated calcium carbonate (100 mg) as an acid suppressor×3 times/day to the patient, was initiated.

Figure 10:
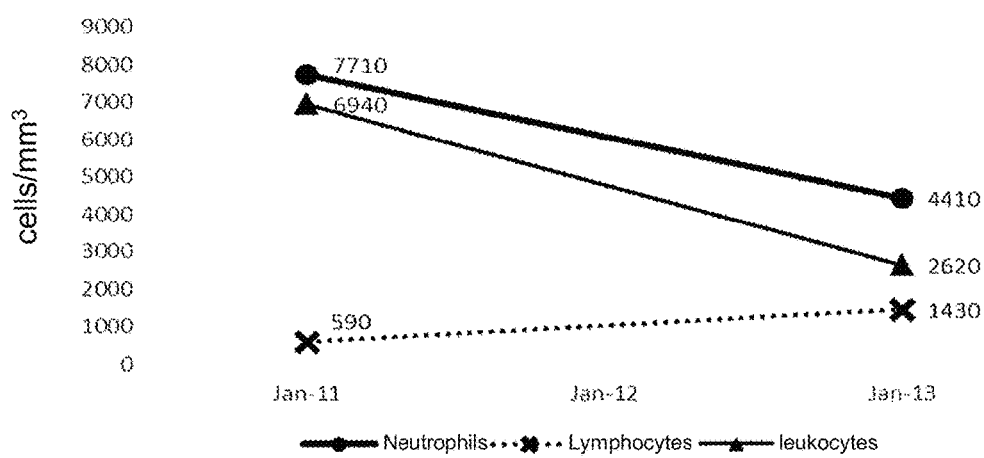
FIG. 10 includes a graph (A) showing the levels of cancer inflammation markers (white blood cell count, neutrophil count, CRP) in the blood, the level of immunity improvement markers (lymphocyte count) and N/L ratio measured with time after a gastrointestinal medicine containing Taxotere and sodium hydrogen carbonate were administered to a female patient (45 years old) diagnosed with breast cancer; and photographs showing chest CT images (B). The white arrows indicate tumors (B).
Figure 10:
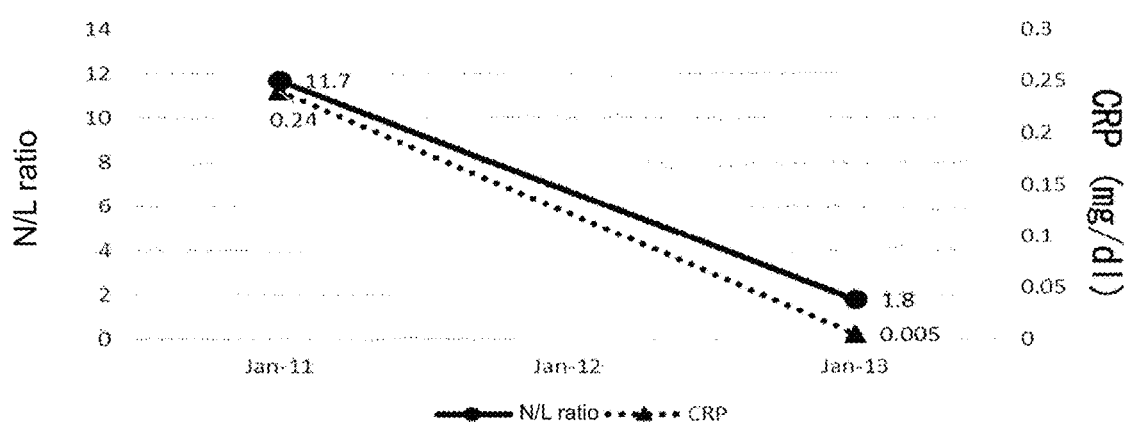
Figure 10:

As a result, white blood cell count and neutrophil count and CRP serving as indexes for cancer inflammation decreased; whereas, lymphocyte count serving as an index of immunity improvement increased. The ratio of neutrophil count/lymphocyte count (N/L) serving as an index for good prognosis, decreased (FIG. 10 (A)) and reduction of a tumor was observed (FIG. 10 (B)). After that, the disease became stable. Then, on and after January, 2013, the patient did not receive administration of Taxotere for two years or more but continuously received the urinary alkalinization therapy. Generally, most of the patients having metastasis of breast cancer to the lung die within a year although the period varies depending on the application or non-application of a chemotherapy and the like. Nevertheless, in the above patient, development of another cancer and recurrence/metastasis have not been confirmed up to present. The result is unpredictable from common technical knowledge on disease condition and survival period of general breast cancer patients having lung metastasis and regarded as an effect, i.e., a therapeutic effect and remission effect, based on administration of a urinary alkalinization agent according to the present invention.

[Example 12] Patient (Female, 54 Years Old) with Recurrent Breast Cancer

A patient (female, 54 years old) was diagnosed with breast cancer in April, 2001, underwent a surgery for partially removing the left breast in July of the same year and received a radiation therapy in August of the same year. Thereafter, the patient continuously received a hormonal therapy (Aromasin (trade name) (exemestane)) for the following two years. Recurrence of breast cancer was observed in August, 2011 and metastasis to the right lung was found in January, 2016.

To the patient, a hormonal agent for breast cancer, tamoxifen (20 mg/day), was administered from August, 2016; at the same time, a urinary alkalinization therapy including daily oral intake of sodium hydrogen carbonate (6 g/day) and a plum extract containing 1 g or more of citric acid (15 g/day), was initiated.

Figure 11:
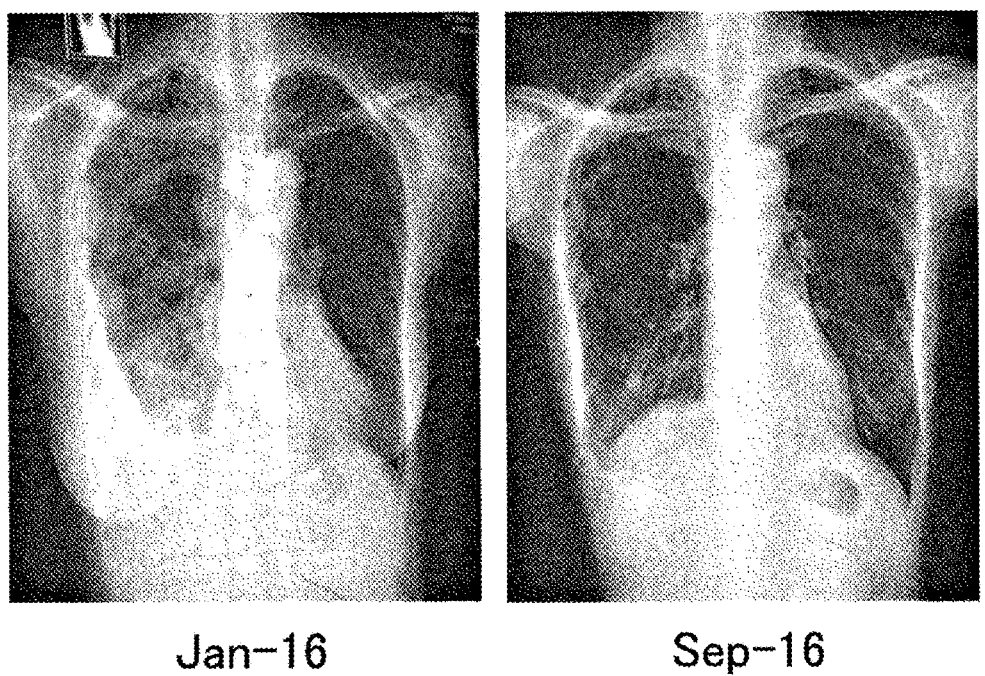
FIG. 11 includes chest X-ray photographs (A) of a female patient (54 years old) diagnosed with recurrent breast cancer before and after administration of tamoxifen and intake of sodium hydrogen carbonate and a plum extract; and a graph (B) showing the levels of tumor markers (BCA225, CA15-3 and CEA) in the blood measured with time.
Figure 11:
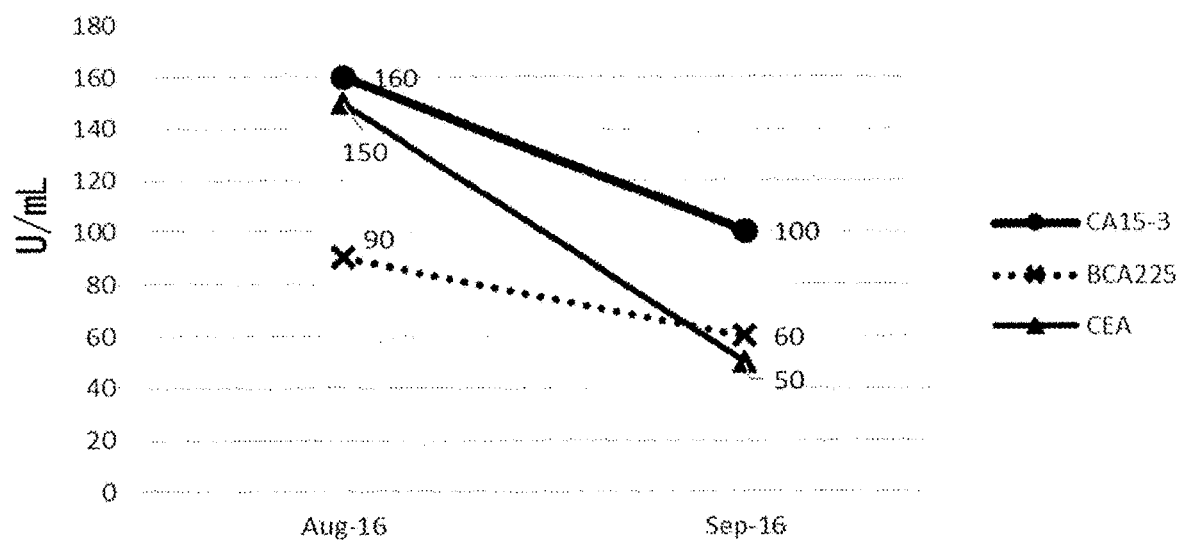

As a result, urine pH value was alkalinized (pH value 7 to 8) and then maintained at the same value (no data shown); the amount of the pleural effusion decreased (FIG. 11 (A)); and the levels of tumor markers (BCA225, CA15-3 and CEA) in the blood decreased (FIG. 11 (B)). The urinary alkalinization therapy has been continued and development of another cancer and recurrence/metastasis have not been confirmed. As mentioned above, most of the patients having metastasis of breast cancer to the lung die within a year although the period varies depending on the application or non-application of a chemotherapy and the like. Nevertheless, in the above patient, development of another cancer and recurrence/metastasis have not been confirmed up to present. The result is unpredictable from common technical knowledge on disease condition and survival period of general breast cancer patients having lung metastasis and regarded as an effect, i.e., a therapeutic effect and remission effect, based on administration of a urinary alkalinization agent according to the present invention.

[Example 13] Gastric Cancer Patient (Male, 91 Years Old)

Figure 12:
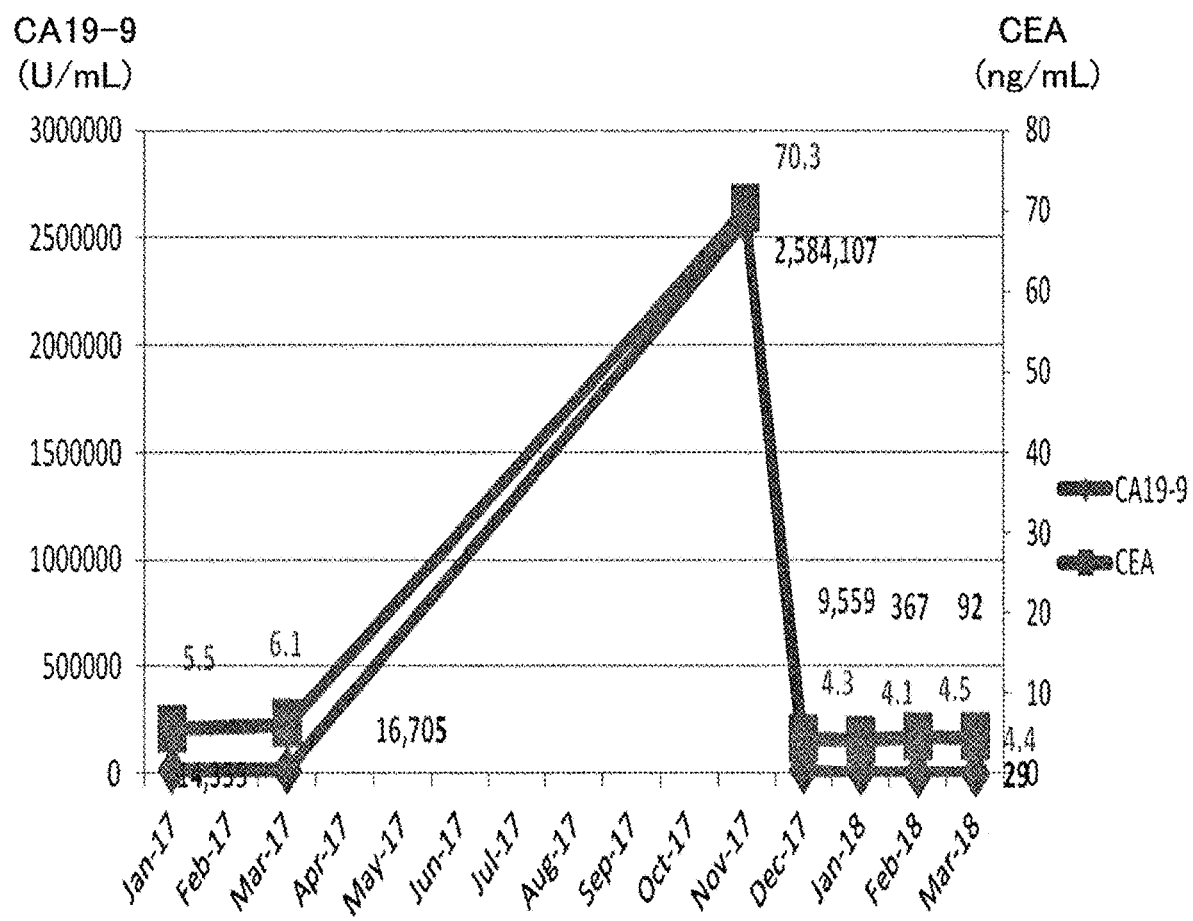
FIG. 12 is a graph showing the levels of tumor markers (CA19-9 and CEA) in the blood measured with time before and after alkalinization (pH7.0 or more) of urine by administration of sodium bicarbonate and administration of Opdivo (registered trademark) to a male patient (91 years old) diagnosed with Stage IV advanced gastric cancer associated with multiple liver metastases and lung metastasis.
Figure 13:
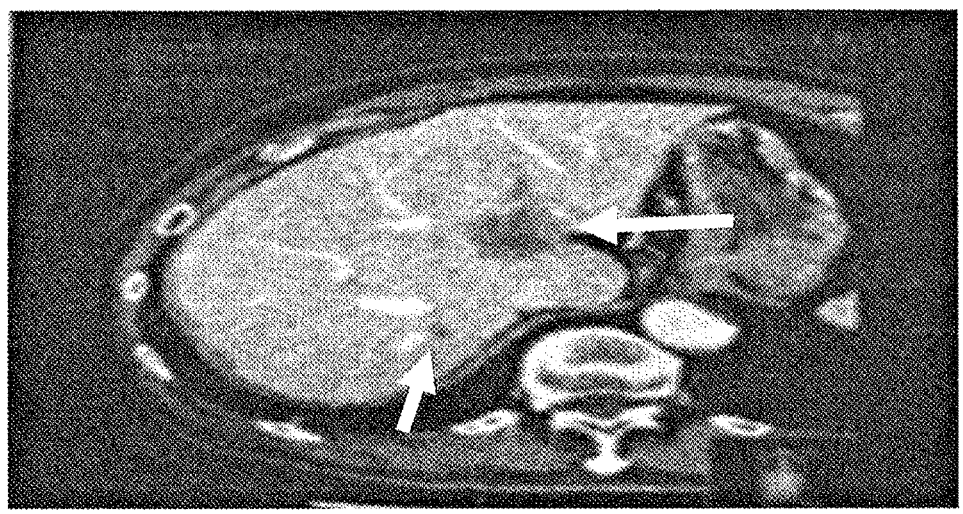
FIG. 13 shows photographs of CT images of the liver before and after alkalinization (pH7.0 or more) of urine by administration of sodium bicarbonate and administration of Opdivo (registered trademark) to a male patient (91 years old) diagnosed with Stage IV advanced gastric cancer associated with multiple liver metastasis and lung metastasis: (A) shows liver metastases of gastric cancer before sodium bicarbonate and Opdivo (registered trademark) were administered (sites indicated by the arrows); and (B) disappearance of liver metastases of gastric cancer after sodium bicarbonate and Opdivo (registered trademark) were administered (site enclosed by a circle indicates a primary lesion (gastroesophageal junction).
Figure 13:

A patient (male, 91 years old) was diagnosed, in January 2017, with advanced gastric cancer (Stage IV (associated with multiple liver metastases and lung metastasis)) having a primary lesion in the gastroesophageal junction. A standard therapy in Japan for advanced recurrent gastric cancer, SOX therapy (TS-1 (trade name) (combination drug of tegafur/gimeracil/oteracil potassium) 120 mg/individual, 14 daily administration 14 day off; Elplat (trade name) (oxaliplatin) 170 mg, once per 3 weeks) was started from the middle of February, 2017. However, due to severe fatigue, the dose of TS-1 was reduced to 100 mg/individual in the middle and the therapy was continued. Nevertheless, no shrinkage of the primary lesion was observed; on the contrary, the number of metastatic cancers increased in the liver and enlarged (FIG. 13 (A)). In addition, the levels of tumor markers, CA19-9 and CEA, continuously increased (FIG. 12).

Then, the SOX therapy was stopped from November 2017 and a urinary alkalinization therapy including daily oral administration of 5 tablets of Mylan (trade name) (sodium bicarbonate tablets, 500 mg)×2 times/day, was initiated; at the same time, Opdivo (trade name) (nivolumab) was administered in a dose of 3 mg/kg (body weight) at the intervals of 2 weeks.

As a result, it was confirmed that the urine pH value was alkalinized and was maintained at pH7 to 7.5. It was also confirmed that the blood level of a tumor marker, CEA, decreased from 70.3 ng/mL (November, 2017) to 4.3 ng/mL (March, 2018) and the blood level of CA19-9 decreased from 2,584,107 U/mL (November, 2017) to 29 U/mL (March, 2018) (FIG. 12). It was further confirmed that a primary lesion gastric cancer in the gastroesophageal junction and a number of metastatic cancers to the liver disappeared (FIG. 13 (B)). The urinary alkalinization therapy has been continued and development of another cancer and recurrence/metastasis have not been confirmed.

Generally, the five year survival rate of an advanced and/or an end-stage gastric cancer patient (70's, male, Stage III) is reported as about 7.1% even though the rate slightly varies depending on the application or non-application of, e.g., a chemotherapy; and the median overall survival of gastric cancer patients (gastroesophageal junction cancer) treated with Opdivo (trade name) was reported as about 5.26 months (Lancet. 2017 Dec. 2; 390 (10111): 2461-2471). The advanced and/or end-stage gastric cancer is still an untreatable disease having no effective therapy, at present. Administration of Opdivo (trade name) contributes to extending a life of a patient with end-stage gastric cancer; however, tumor shrinkage and a decrease of a tumor marker level were seldom confirmed. Nevertheless, in the patient mentioned above, development of another cancer and recurrence/metastasis have not been confirmed up to present. The result is unpredictable from common technical knowledge on disease condition and survival period of general advanced and/or end-stage gastric cancer patients and regarded as an extraordinary effect, i.e., a therapeutic effect and remission effect, based on administration of a urinary alkalinization agent according to the present invention.

[Example 14] Urine pH Change Caused by Intake of Gastrointestinal Medicine Suppressing Production of Acid in the Stomach or Citric Acid Beverage A healthy woman (63 years old) was allowed to take a gastrointestinal medicine suppressing production of acid in the stomach or citric acid beverage in accordance with the following dose and schedule and thereafter, a change of urine pH value was measured with time.
(Dose/Schedule)
(1) 180 g of a citric acid beverage ("Sokko-Genki" manufactured by Meiji) containing citric acid (1 g), sodium citrate and calcium lactate, was allowed to take after a meal, once a day;
(2) 10 mg of a gastrointestinal medicine (Gaster 10 Tablets manufactured by Daiichi Sankyo Healthcare Co., Ltd.)) containing H2 blocker (famotidine) was allowed to take after a meal, once a day;
(3) 15 mg of a gastrointestinal medicine (Takepron OD Tablets, manufactured by Takeda Pharmaceutical Co. Ltd.) containing a proton pump inhibitor (lansoprazole) was allowed to take after a meal, once a day.

Figure 14:
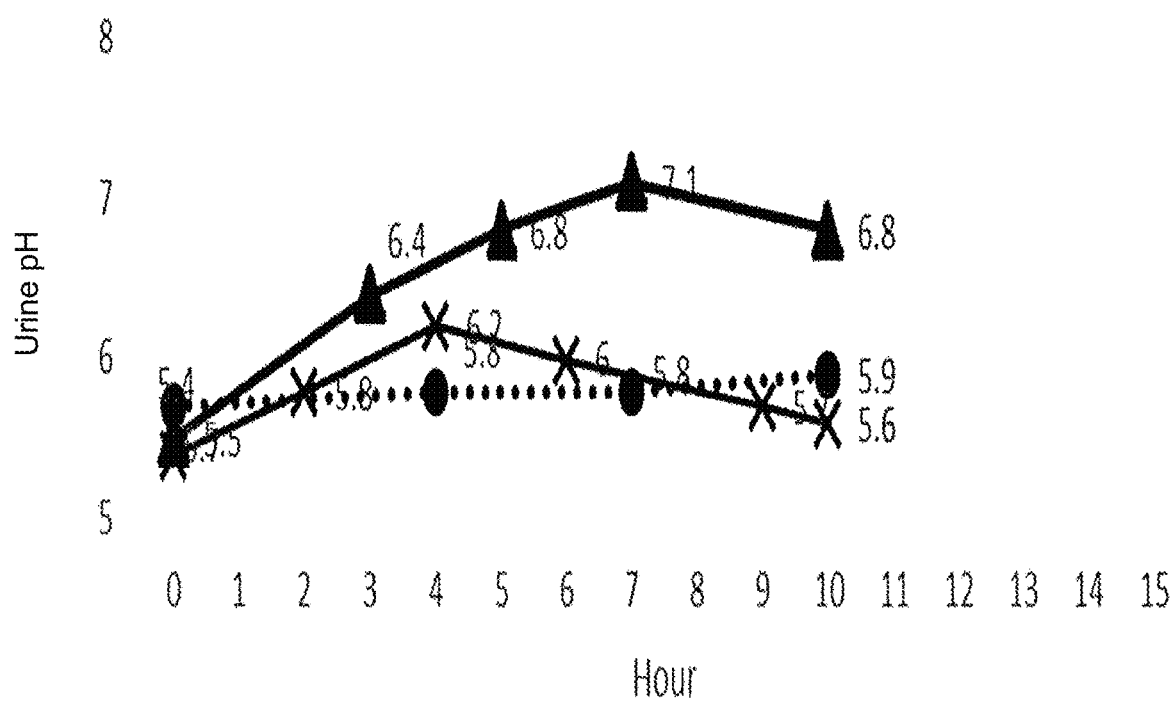
FIG. 14 is a graph showing the urine pH value measured with time after (1) a citric acid beverage containing citric acid, sodium citrate and calcium lactate, (2) a gastrointestinal medicine containing H2 blocker (famotidine) suppressing production of acid in the stomach and (3) a gastrointestinal medicine containing a proton pump inhibitor (lansoprazole) suppressing production of acid in the stomach were separately administered to a healthy woman (63 years old).

The measurement results of urine pH value after taking individual beverage and medicines are shown in FIG. 14. In both administration cases of (2) the gastrointestinal medicine containing H2 blocker and (3) the gastrointestinal medicine containing a proton pump inhibitor, a change in the urine pH value was low and the urine pH value did not reach 7.0 or more. In contrast, in the administration case of (1) citric acid beverage, the urine pH value increased up to 7.1.

These results show that the relationship between gastric acid secretion suppression effect and urinary alkalinization is weak; and that an alkali component such as citric acid, sodium citrate and calcium lactate not only neutralizes gastric acid but also contributes alkalinization of the urine.

[Example 15] Antitumor Effect of Combination Use of Urinary Alkalinization Agent and Cancer Immunotherapeutic Agent (Anti PD-1 Antibody)

C57BL/6 mice (5 weeks old, female) under anesthesia with 2,2,2-tribromoethanol (Avertin; Sigma-Aldrich) were subcutaneously transplanted with B16 mouse melanoma cells ($2 \times 10^6$ cells/mouse).

The resultant mice were randomly divided into the following 4 groups (n=10 per group).
Administration Group:
(1) Control: no treatment;
(2) Urinary alkalinization agent: sodium hydrogen carbonate+magnesium oxide;
(3) cancer immunotherapeutic agent: anti-mouse PD-1 antibody (Bio X Cell, BE0146);
(4) urinary alkalinization agent+cancer immunotherapeutic agent: sodium hydrogen carbonate+magnesium oxide+ anti-mouse PD-1 antibody.
Dosing Schedule:
The urinary alkalinization agent was orally administered every day from two days before the day (Day 0) at which cells were transplanted until test completion date (Day 15 after transplantation of cells). Sodium hydrogen carbonate was administered as a dose of 10 mg/day; and magnesium oxide at a dose of 3.3 mg/day (sodium hydrogen carbonate: magnesium oxide (weight ratio)=3:1).

The cancer immunotherapeutic agent was intraperitoneally administered only once at a dose of 5 mg/kg/day on the following day (Day 1) of transplantation of the cells.

Evaluation Method:

The diameter of tumors was measured twice a week. The antitumor effect was evaluated by calculating tumor volumes.

A body weight was measured twice a week. Toxicity was evaluated based on a change in body weight as an index.

Further, urine was sampled twice a week (one or two hours after administration of a urinary alkalinization agent) and urine pH was measured by pH test paper.

Figures 1, 15:
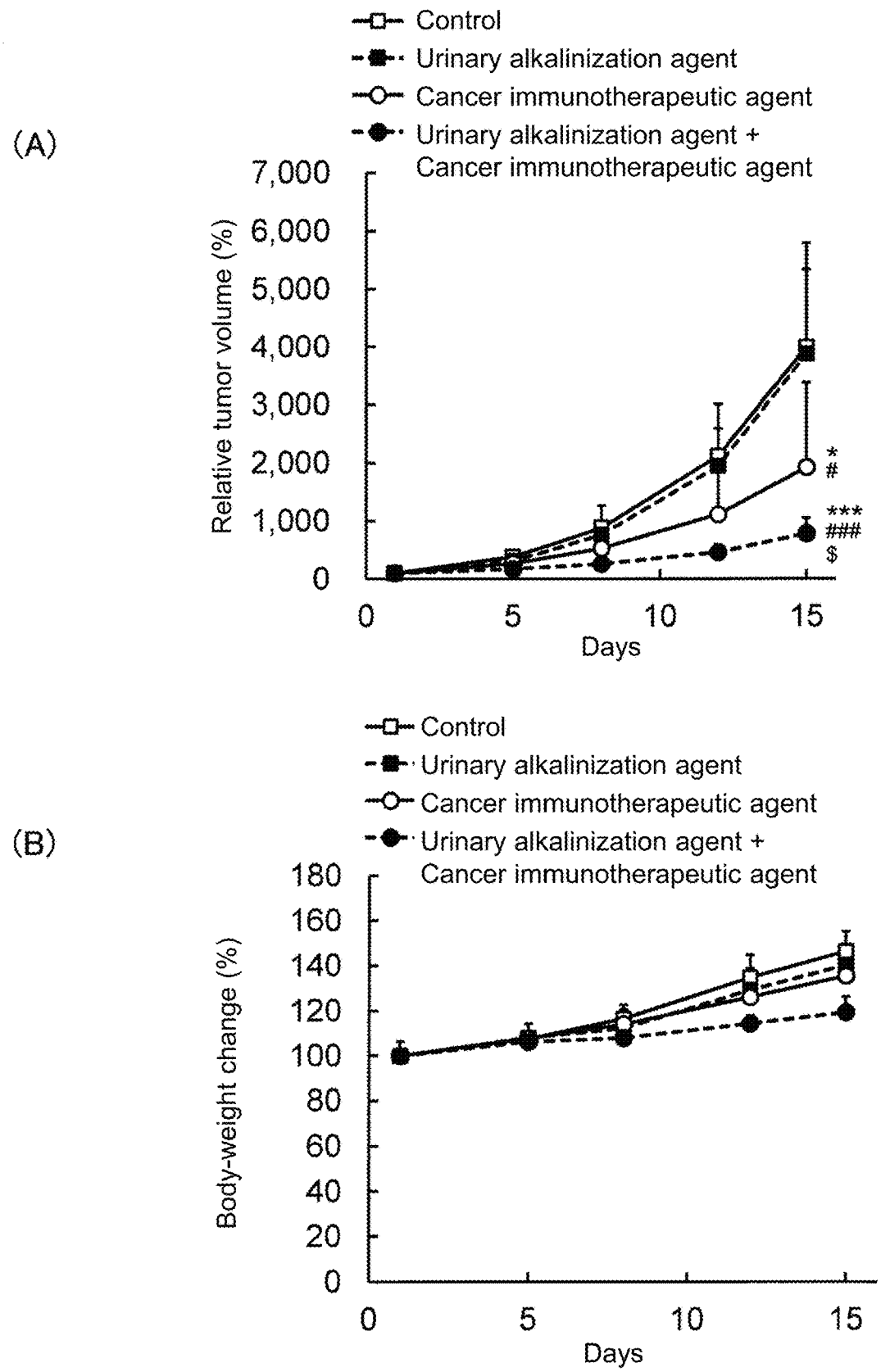
Figure 15:
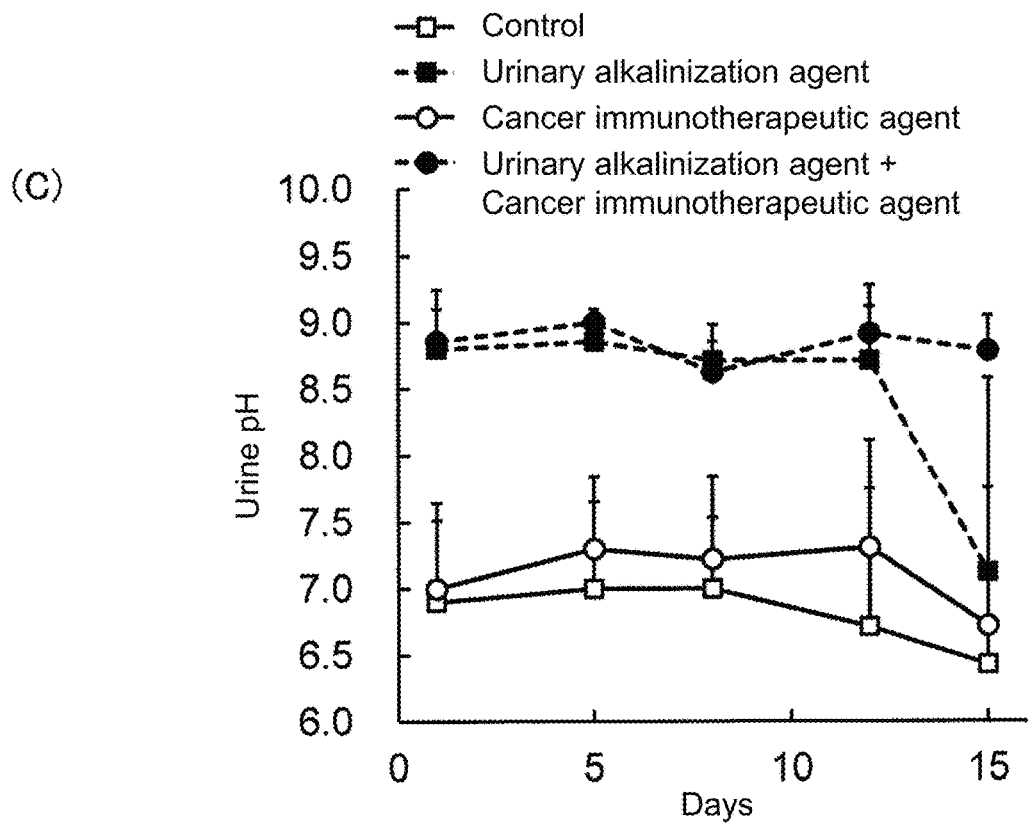
Figure 2:
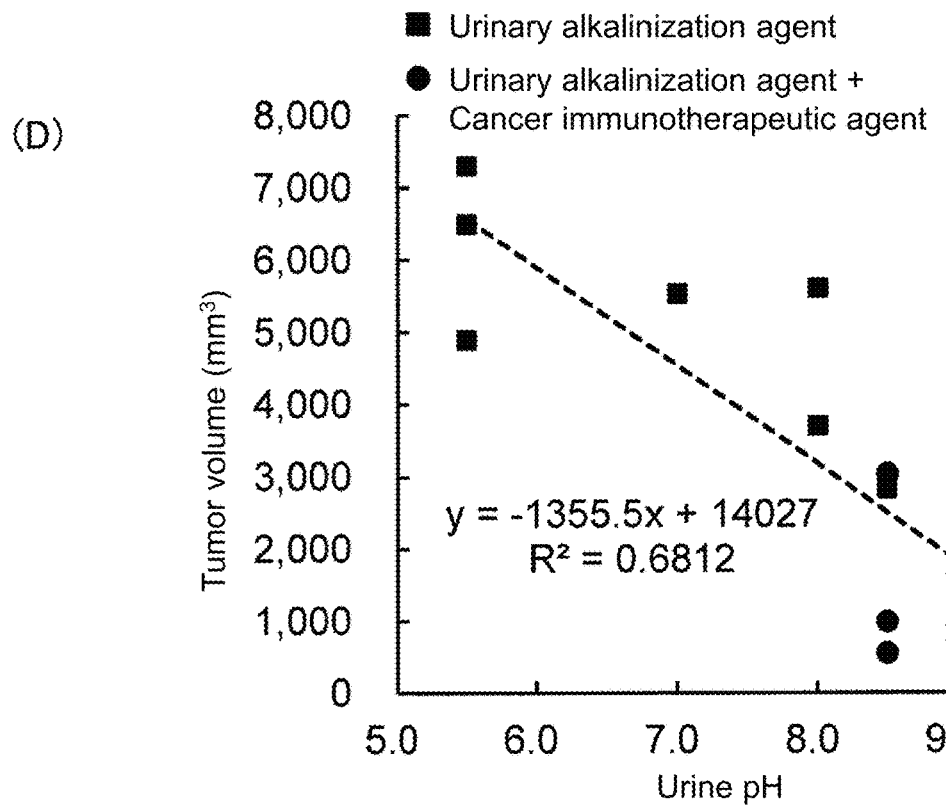

Results:

Individual evaluation results are shown in FIGS. 15-1 and 15-2.

Generally, the growth rate of an animal tumor tends to be significantly high compared to a human tumor. A remarkable effect, such as a reduction of tumor volume, was not observed in the case of single administration of the urinary alkalinization agent (FIG. 15-1 (A), solid square).

However, in the case of combination use of the urinary alkalinization agent and the cancer immunotherapeutic agent compared to the case of using the urinary alkalinization agent alone or a cancer immunotherapeutic agent alone, a tumor volume significantly reduced (FIG. 15-1 (A), solid circle).

With respect to a change in body weight, a significant difference between the individual administration groups was not observed (FIG. 15-1 (B)). From this, it was confirmed that the combination therapy of the urinary alkalinization agent and the cancer immunotherapeutic agent is low in toxicity.

In the group, to which the urinary alkalinization agent was administered or the urinary alkalinization agent and cancer immunotherapeutic agent were administered, the urine pH value was maintained in the alkali pH range (FIG. 15-2 (C), solid square, solid circle). On the final day of the test (Day 15 after transplantation of the cells), it was confirmed that higher the urine pH value, the smaller the tumor volume.

The doses of sodium hydrogen carbonate and magnesium oxide used in this method correspond to clinically accepted doses to humans. It was confirmed that the effect obtained by combined administration of the urinary alkalinization agent, which contains sodium hydrogen carbonate and magnesium oxide in the above doses, and the cancer immunotherapeutic agent (an anticancer drug) is a synergistic effect. The result is not contradictory to the therapeutic result of human cancer patients obtained by using the aforementioned urinary alkalinization therapy and an anti-cancer agent. The efficacy of the oral administration of the urinary alkalinization agent at a clinical acceptable dose to humans was confirmed.

[Example 16] Antitumor Effect of Combination Use of Urinary Alkalinization Agent and Cancer Immunotherapeutic Agent (Lentinan) on a Postoperative Recurrence Case of Scirrhous Gastric Cancer A patient (male, 74 years old) was diagnosed with gastric cancer in February, 2012 and underwent surgical resection of ⅔ stomach. Thereafter (November, 2013), abnormality was found in the stomach and total gastrectomy was carried out in January, 2014. The patient was diagnosed with scirrhous gastric cancer. A therapy of administering 40 mg of TS-1 (trade name) (combination drug of tegafur/gimeracil/oteracil potassium)×twice/day (4 week administration, 2 week drug holiday) was initiated but canceled since the patient experienced a side effect. Significant elevation of the level of tumor marker CA72-4 was found from around September, 2014, recurrence in the excision site was doubted.

Then, from November, 2014, the dose of TS-1 was extremely reduced (20 mg/week); at the same time, a urinary alkalinization therapy including daily oral administration of sodium bicarbonate (3 g×twice/day) and intravenous administration of lentinan (2 mg/week), were initiated.

Figure 16:
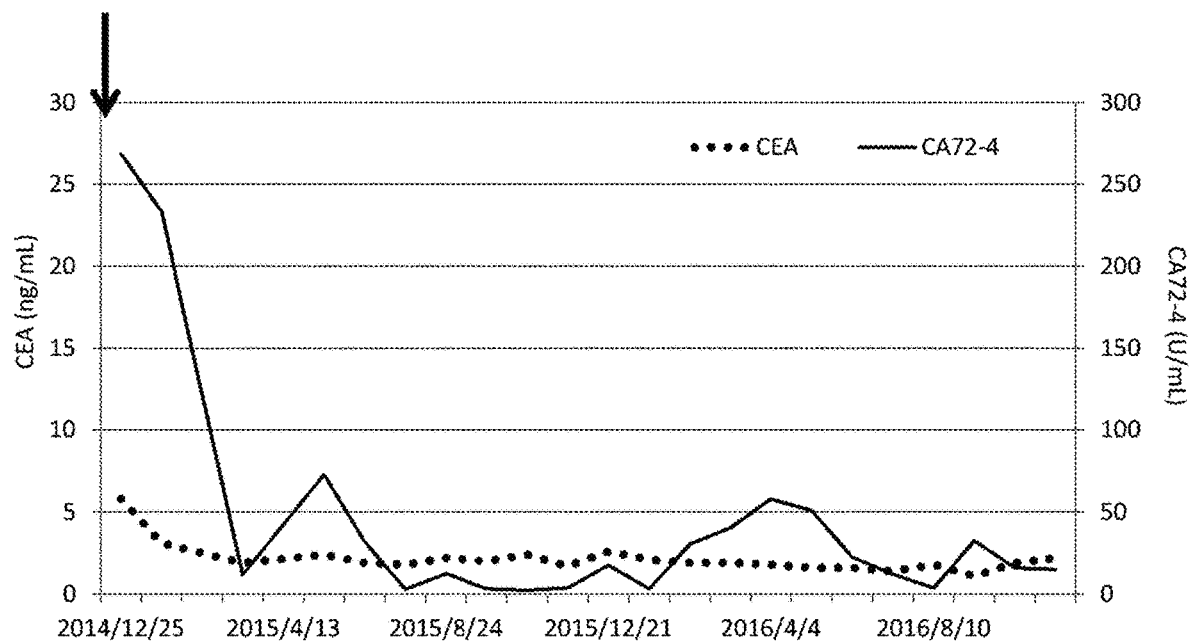
FIG. 16 is a graph showing measurement results of the tumor markers (CA72-4 and CEA) in the blood with time after an extremely low dose of TS-1 (trade name) (a combination drug of Tegafur/gimeracil/oteracil potassium), sodium bicarbonate and lentinan were administered to a patient (male, 74 years old) (postoperative recurrence) diagnosed with scirrhous gastric cancer. The arrow indicates the initiation of administration of TS-1, sodium bicarbonate and lentinan.

As a result, the urine pH value was alkalinized (neutral to alkali pH range) and the levels of tumor markers CA72-4 and CEA both significantly decreased and thereafter were maintained within normal ranges (FIG. 16). The urinary alkalinization therapy and administration of TS-1 and lentinan have been continued and development of another cancer and recurrence/metastasis have not been confirmed.

[Example 17] Antitumor Effect of Combination Use of Urinary Alkalinization Agent and Cancer Immunotherapeutic Agent (Lentinan) on Postoperative Recurrence Case of Gastric Cancer A patient (male, 68 years old) had stomachache from around 2008, threw up blood in April, 2015 and diagnosed with cardiac cancer of the stomach (pT3N1M0, Stage IIB) by an emergency room doctor. The patient had total gastrectomy and cholecystectomy. Thereafter, elevation of the levels of tumor markers CA72-4 and CEA was observed, and recurrence was doubted. Then, a urinary alkalinization therapy including daily oral administration of sodium bicarbonate (3 g×twice/day) and intravenous administration of TS-1 (20 mg/week) and lentinan (2 mg/week) extremely reduced in doses, were initiated from July, 2015.

Figure 17:
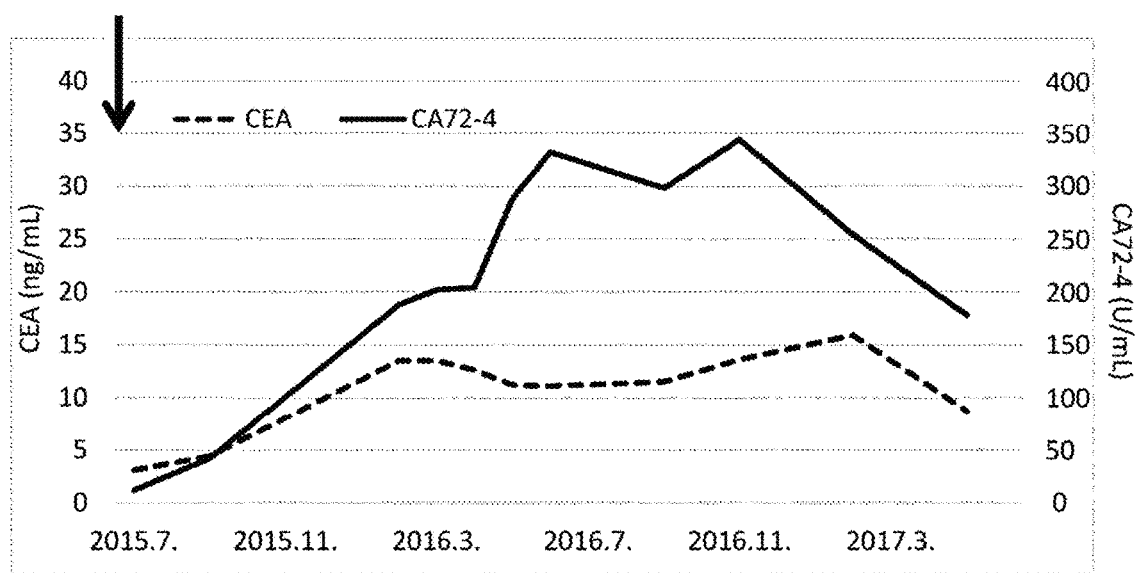
FIG. 17 is a graph showing measurement results of the tumor markers (CA72-4 and CEA) in the blood with time after an extremely low dose of TS-1, sodium bicarbonate and lentinan were administered to a patient (male, 74 years old) (postoperative recurrence) diagnosed with gastric cardia cancer (pT3N1M0, Stage IIB). The arrow indicates the initiation of administration of TS-1, sodium bicarbonate and lentinan.

As a result, urine pH value was alkalinized and maintained at about pH 8.0. Further, decreases both in levels of the tumor markers CA72-4 and CEA were confirmed (FIG. 17). Urinary alkalinization therapy, and administration of TS-1 and lentinan have been continued and development of another cancer and recurrence/metastasis have not been confirmed.

[Example 18] Antitumor Effect of Combination Use of Urinary Alkalinization Agent and Cancer Immunotherapeutic Agent (Lentinan) on Gastric Corpus Cancer A patient (male, 55 years old) was diagnosed with gastric corpus cancer (T2N1M0, Stage IIA) in April, 2017. Since the patient refused both surgical operation and intensified chemotherapy for cancer, a urinary alkalinization therapy including daily oral administration of sodium bicarbonate (3 g×twice/day) and intravenous administration of TS-1 (20 mg/week) and lentinan (2 mg/week) extremely reduced in doses, were initiated.

Figure 18:
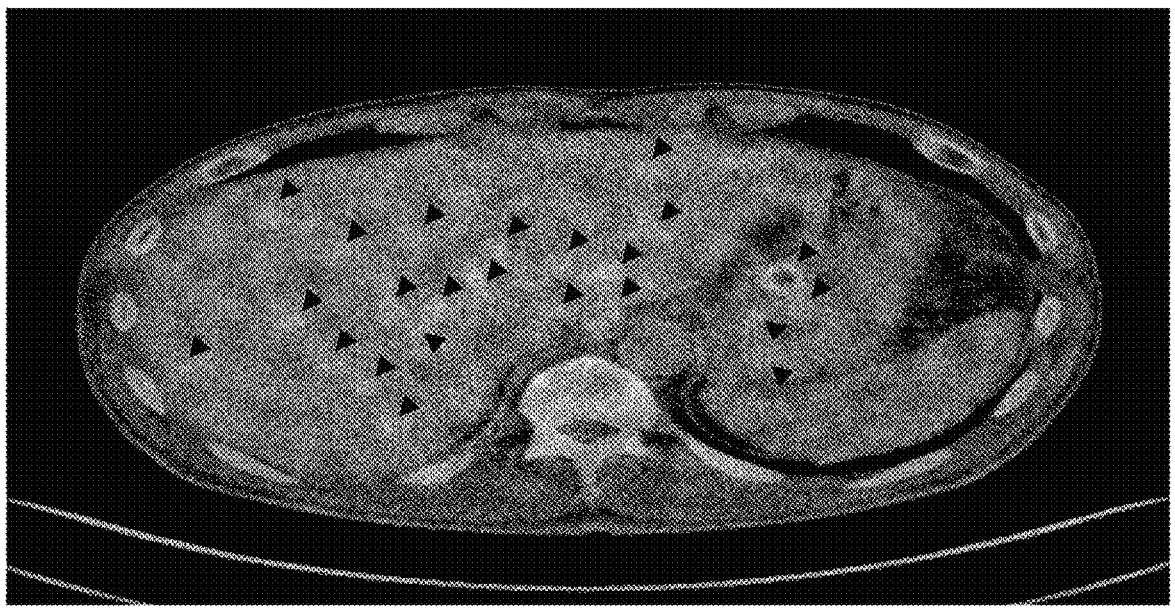
FIG. 18 shows photographs showing PET/CT images of a patient (male, 55 years old) diagnosed with gastric corpus cancer (T2N1M0, Stage IIA) before (A) and after (B) administration of an extremely low dose of TS-1, sodium bicarbonate and lentinan. The black arrow-head indicates a main tumor site.
Figure 18:
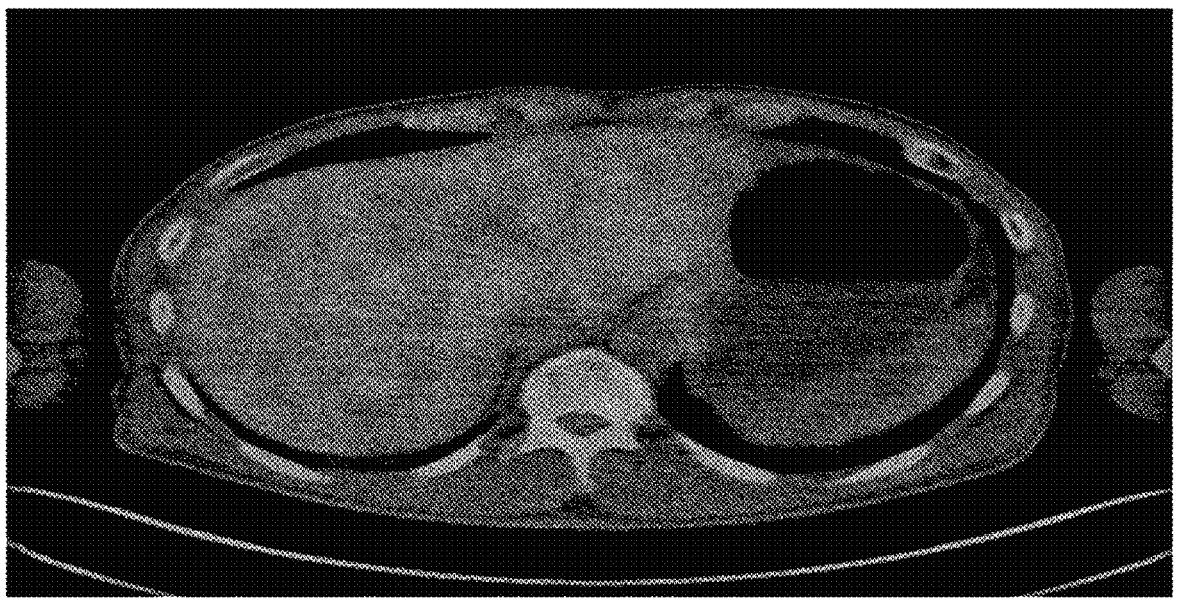

As a result, many tumor sites observed in gastric endoscope images and PET/CT images disappeared after about a year (FIG. 18). During the period, bad smell, which is probably caused by necrosis of cancer cells, was sensed in exhalation from the cancer patient. Two months after the initiation of the therapy, the level of a tumor marker, CA72-4 dropped from 9.3 to 4.1; lymphocyte count increased from 1550 to 1690; and urine pH was maintained at about 8.5. Urinary alkalinization therapy, and administration of TS-1 and lentinan have been continued and development of another cancer and recurrence/metastasis have not been confirmed.

[Example 19] Antitumor Effect of Combination Use of Urinary Alkalinization Agent and Cancer Immunotherapeutic Agent (Lentinan) on Rectal Cancer (after Surgery)

To a postoperative patient (male, 69 years old) with rectal cancer (Stage IIIB), a urinary alkalinization therapy including daily oral administration of sodium bicarbonate (5 g×twice/day); administration of TS-1 (40 mg×twice/day; 4 week administration, 2 week drug holiday); and intravenous administration of lentinan (2 mg/week) were initiated after the surgery (November, 2017).

Figure 19:
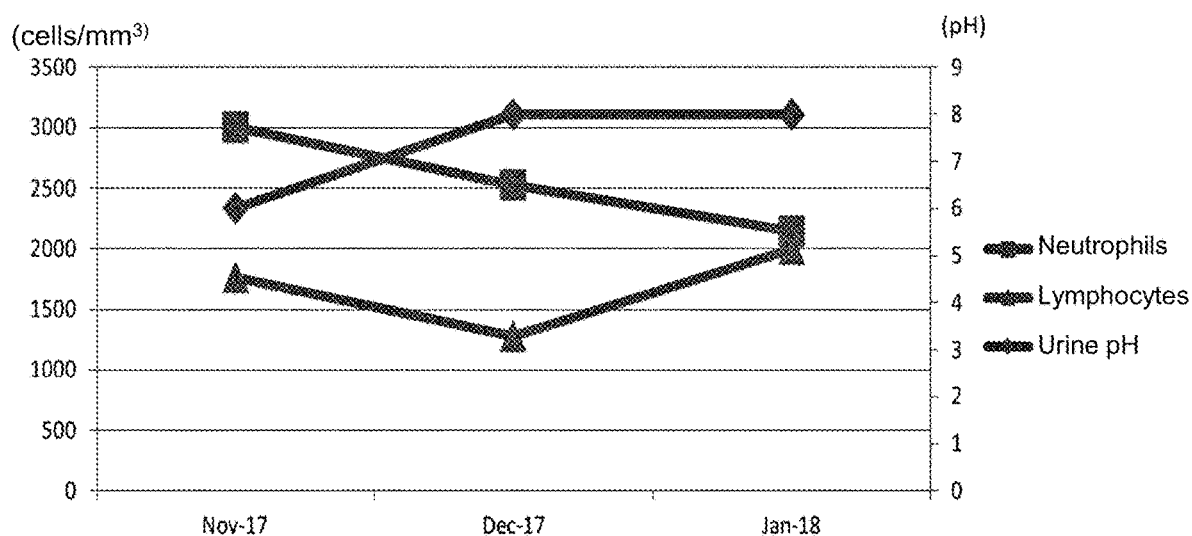
FIG. 19 is a graph showing the measurement results of urine pH value, lymphocyte count and neutrophil count with time after TS-1, sodium bicarbonate and lentinan were administered to a postoperative patient (male, 69 years old) with rectal cancer (Stage IIIB).

As a result, urine pH value was alkalinized and maintained at about pH 8.0. The lymphocyte count indicating immunity improvement increased; and neutrophil count decreased indicating improvement of cancer inflammation (FIG. 19). These results show that recurrence of cancer is suppressed and suggest that this therapy has a cancer recurrence prevention effect.

As mentioned in the foregoing, it was confirmed that the pH value of urine can be changed by administration of a urinary alkalinization agent, thereby alkalinizing the urine. It was also confirmed that medicines conventionally used as gastrointestinal medicines and laxatives can be used as a urinary alkalinization agent as mentioned above. It was further confirmed that the administration route of a urinary alkalinization agent is not limited to the oral one; that transdermal administration can be also used for changing the pH value to alkalinize the urine; and that administration can be made by taking a bath, i.e., getting in hot water containing a urinary alkalinization agent. As a result, it is demonstrated that a commercially available gastrointestinal medicine and laxative containing a predetermined component and a bath additive containing a predetermined component can be used as a urinary alkalinization agent.

It was clearly shown that administration of a urinary alkalinization agent is effective for treating cancer, and particularly, can prevent cancer recurrence and metastasis and is effective for extending the life of patients. It was also clearly shown that combined administration of a urinary alkalinization agent and an anti-cancer agent (for example, a cancer immunotherapeutic agent such as an anti PD-1 antibody and lentinan) can provide a high antitumor effect.

The invention claimed is:

1. A method for treatment of a cancer, comprising orally administering for an entire period of said treatment an effective cancer treating amount of a urinary alkalinization agent comprising (a) sodium hydrogen carbonate and (b) magnesium oxide or citric acid or a salt thereof to a patient with the cancer in need thereof with administering for the entire period of said treatment an anti-cancer agent, wherein said administering the effective cancer treating amount of the urinary alkanization agent comprises orally administering 1 g to 20 g a day of the sodium hydrogen carbonate and 1 g to 20 g a day of the magnesium oxide or the citric acid, wherein said administering results in at least one of prevention of recurrence of the cancer in the patient, prevention of metastasis of the cancer in the patient or an extension of the life of the patient, wherein only the urinary alkalinization agent is administered via the oral administration route during the entire period of said treatment, wherein the anti-cancer agent is an anti PD-1 antibody or lentinan.

2. The method according to claim 1, in which the anti-cancer agent is an anti PD-1 antibody.

3. The method according to claim 1, in which the cancer is lung cancer, lymphoma, pancreatic cancer, breast cancer, gastric cancer or rectal cancer.

4. The method according to claim 2, wherein the urinary alkalinization agent comprises (a) the sodium hydrogen carbonate and (b) the magnesium oxide.

5. The method according to claim 1, wherein said administering the effective cancer treating amount of the urinary alkanization agent comprises orally administering (a) 1 g to 20 g a day of the sodium hydrogen carbonate and (b) 1 g to 20 g a day of the citric acid or a salt thereof.

6. The method according to claim 1, wherein the anti-cancer agent is lentinan.

7. The method according to claim 1, wherein said administering the effective cancer treating amount of the urinary alkanization agent comprises orally administering (a) 1 g to 20 g a day of the sodium hydrogen carbonate and (b) 1 g to 20 g a day of the magnesium oxide.

8. The method according to claim 7, wherein the cancer is gastric lymphoma.

9. The method according to claim 8, wherein said administering results in disappearing of the gastric lymphoma in the patient.

10. The method according to claim 5, wherein the cancer is pancreatic cancer.

11. The method according to claim 10, wherein the patient has the pancreatic cancer with liver metastasis and wherein said administering results in disappearing of the liver metastasis in the patient.

12. The method according to claim 7, wherein the cancer is lung cancer.

13. The method according to claim 12, wherein said administering results in a decrease in a blood level of a CEA tumor marker in the patient.

14. The method according to claim 7, wherein the cancer is malignant lymphoma.

15. The method according to claim 14, wherein said administering results in normalizing of a CRP inflammation marker level in the patient.

16. The method according to claim 5, wherein the cancer is breast cancer.

17. The method according to claim 16, wherein said administering results in a decrease in a blood level of a tumor marker in the patient, wherein the marker is selected from BCA225, CA15-3 and CEA.

18. A method for treatment of a cancer, comprising orally administering for an entire period of said treatment an effective cancer treating amount of a urinary alkalinization agent comprising (a) sodium hydrogen carbonate and (b) citric acid or a salt thereof to a patient with the cancer in need thereof with administering for the entire period of said treatment an anti-cancer agent, wherein said administering the effective cancer treating amount of the urinary alkanization agent comprises orally administering 1 g to 20 g a day of the sodium hydrogen carbonate and 1 g to 20 g a day the citric acid or a salt thereof, wherein said administering results in at least one of prevention of recurrence of the cancer in the patient, prevention of metastasis of the cancer in the patient or an extension of the life of the patient, wherein only the urinary alkalinization agent is administered via the oral administration route during the entire period of said treatment, wherein the cancer is pancreatic cancer or breast cancer.

19. The method according to claim 18, in which the anti-cancer agent is an anti PD-1 antibody.

20. The method according to claim 18, wherein the anti-cancer agent is lentinan.

21. The method according to claim 18, wherein the cancer is pancreatic cancer.

22. The method according to claim 21, wherein the patient has the pancreatic cancer with liver metastasis and wherein said administering results in reduction of the liver metastasis in the patient.

23. The method according to claim 18, wherein the cancer is breast cancer.

24. The method according to claim 23, wherein said administering results in a decrease in a blood level of a tumor marker in the patient, wherein the marker is selected from BCA225, CA15-3 and CEA.

* * * * *